United States Patent
Vogt et al.

(10) Patent No.: US 12,102,784 B2
(45) Date of Patent: Oct. 1, 2024

(54) IMPLANT FOR LOCAL ACTIVE INGREDIENT RELEASE

(71) Applicant: Heraeus Medical GmbH, Wehrheim (DE)

(72) Inventors: Sebastian Vogt, Wehrheim (DE); Thomas Kluge, Wehrheim (DE)

(73) Assignee: Heraeus Medical GmbH, Wehrheim (DE)

( * ) Notice: Subject to any disclaimer, the term of this patent is extended or adjusted under 35 U.S.C. 154(b) by 0 days.

(21) Appl. No.: 17/474,961

(22) Filed: Sep. 14, 2021

(65) Prior Publication Data
US 2022/0105325 A1 Apr. 7, 2022

(30) Foreign Application Priority Data
Oct. 2, 2020 (EP) ..................................... 20199745

(51) Int. Cl.
| | |
|---|---|
| *A61M 31/00* | (2006.01) |
| *A61M 5/178* | (2006.01) |
| *A61M 5/32* | (2006.01) |

(52) U.S. Cl.
CPC ........ *A61M 31/002* (2013.01); *A61M 5/1782* (2013.01); *A61M 5/3286* (2013.01); *A61M 2205/0216* (2013.01)

(58) Field of Classification Search
CPC .............. A61M 31/002; A61M 31/007; A61M 2205/0216; A61M 5/1782; A61M 5/3286
See application file for complete search history.

(56) References Cited

U.S. PATENT DOCUMENTS

| 4,738,657 A | 4/1988 | Hancock et al. |
| 4,784,646 A | 11/1988 | Feingold |
| (Continued) | | |

FOREIGN PATENT DOCUMENTS

| CN | 101052437 | 10/2007 |
| CN | 104721903 | 6/2015 |
| (Continued) | | |

OTHER PUBLICATIONS

Extended European Search Report mailed Mar. 24, 2021 by the European Patent Office for priority European patent application No. 20199745.9.

(Continued)

*Primary Examiner* — Philip R Wiest
*Assistant Examiner* — Matthew Wrubleski
(74) *Attorney, Agent, or Firm* — Dicke, Billig & Czaja, PLLC

(57) ABSTRACT

The invention relates to an implant for local active ingredient release having an upper wall (1), which is closed and disk-shaped and consists of a material which is pierceable with an injection cannula using a force of less than 100 N, is self-sealing and is elastically deformable, a lower wall (2) which is arranged opposite the upper wall (1), is disk-shaped, is elastically deformable and has at least one liquid-permeable feed-through (3) through the lower wall (2), a hollow space (4) which is arranged between the upper wall (1) and the lower wall (2), and an anti-piercing means (6), which is disk-shaped, between the upper wall (1) and the lower wall (2), wherein the anti-piercing means (6) consists of a material which is not pierceable with an injection cannula (100) using a force of less than 100 N.
The invention also relates a method for filling such an implant with a liquid.

15 Claims, 33 Drawing Sheets

(56) References Cited

U.S. PATENT DOCUMENTS

| | | | |
|---|---|---|---|
| 4,904,241 A * | 2/1990 | Bark | A61M 39/0208 604/117 |
| 5,102,389 A | 4/1992 | Hauser | |
| 5,637,088 A * | 6/1997 | Wenner | A61M 39/0208 604/93.01 |
| 5,660,846 A * | 8/1997 | Cheikh | A61K 9/70 514/772.3 |
| 5,681,289 A | 10/1997 | Wilcox et al. | |
| 5,954,687 A | 9/1999 | Baudino | |
| 6,013,051 A | 1/2000 | Nelson | |
| 6,186,982 B1 * | 2/2001 | Gross | A61M 5/155 604/93.01 |
| 6,245,111 B1 | 6/2001 | Shaffner | |
| 6,852,106 B2 | 2/2005 | Watson et al. | |
| 7,731,700 B1 * | 6/2010 | Schytte | A61M 39/04 604/288.03 |
| 7,985,207 B2 | 7/2011 | Paganon | |
| 9,504,810 B2 | 11/2016 | Cheng | |
| 11,129,936 B2 | 9/2021 | Gibson et al. | |
| 11,241,266 B2 | 2/2022 | Vogt et al. | |
| 11,511,073 B2 | 11/2022 | Vogt et al. | |
| 2002/0138068 A1 | 9/2002 | Watson et al. | |
| 2003/0139811 A1 | 7/2003 | Watson et al. | |
| 2004/0049159 A1 * | 3/2004 | Barrus | A61B 5/150572 604/174 |
| 2007/0219471 A1 | 9/2007 | Johnson et al. | |
| 2010/0042213 A1 | 2/2010 | Nebosky et al. | |
| 2015/0174317 A1 | 6/2015 | Momose | |
| 2016/0128726 A1 * | 5/2016 | Malkowski | A61B 17/3494 600/208 |
| 2018/0028320 A1 | 2/2018 | Forsell | |

FOREIGN PATENT DOCUMENTS

| | | | |
|---|---|---|---|
| CN | 111281519 | 6/2020 | |
| DE | 102018218429 | 4/2020 | |
| EP | 0788351 | 2/2003 | |
| EP | 0822844 | 6/2004 | |
| GB | 2290971 A | 1/1996 | |
| TW | 201422264 | 6/2014 | |
| TW | 201742644 | 12/2017 | |
| WO | 85/02123 | 5/1985 | |
| WO | WO-9903527 A1 * | 1/1999 | A61M 39/0208 |
| WO | 2007/084878 A1 | 7/2007 | |
| WO | 2010/088548 A1 | 8/2010 | |
| WO | 2017/178951 A1 | 10/2017 | |

OTHER PUBLICATIONS

Matsukawa A. et al, "Analysis of the Inflammatory Cytokine Network among TNFa, IL-1β, IL-1 Receptor Antagonist, and IL-8 in LPS-Induced Rabbit Arthritis" Lab. Invest. May 1997; 76 (5): 629-638 (PMID: 9166282).

Fong K.Y. et al. "Cytokine concentrations in the synovial fluid and plasma of rheumatoid arthritis patients: Correlation with bony erosions" Clin. Exp. Rheumatol. Jan.-Feb. 1994; 12(1): 55-58 (PMID: 8162643).

Kutukculer N. et al, "Study of Pro-Inflammatory (TNF-a, IL-1a, IL-6) and T-Cell-Derived (IL-2, IL-4) Cytokines in Plasma and Synovial Fluid of Patients with Juvenile Chronic Arthritis: Correlations with Clinical and Laboratory Parameters", Clin. Rheumatol. 1998; 17(4): 288-292 (DOI: 10.1007/BF01451007; PMID: 9776110).

Roux-Lombard P. et al., "Preliminary report on cytokine determination in human synovial fluids: a consensus study of the European Workshop for Rheumatology Research", Clin. Exp. Rheumatol. 1992 10: 515-520 (PMID: 1333926).

Lubberts E. et al. "The role of T-cell interleukin-17 in conducting destructive arthritis: lessons from animal models", Arthritis Res. Ther. 2005; 7(1): 29-37 (DOI: 10.1186/ar1478; Epub Nov. 30, 2004 PMID: 15642151).

* cited by examiner

IMPLANT FOR LOCAL ACTIVE INGREDIENT RELEASE

The invention relates to an implant for local active ingredient release and to a method for filling such an implant with a liquid.

Accordingly, the subject of the present invention is an implant which is intended for local active ingredient release, in particular for local release of immunosuppressants. Once implanted, the implant can be reloaded multiple times with active ingredients by a medical user without the implant having to be explanted for this purpose.

Rheumatic diseases are among the so-called autoimmune diseases, in which, for reasons which are at present not yet precisely understood, the immune system attacks endogenous structures. The diseases rheumatoid arthritis and psoriatic arthritis belong to the rheumatic group of diseases and are associated with joint inflammation (arthritis). This joint inflammation, which usually has a chronic course, can lead to progressive destruction of the joints. Human joints are surrounded by a joint capsule (articular capsule). This capsule is composed of an outer connective tissue layer (*membrana fibrosa*) and an inner layer known as the synovial membrane (*membrana synovialis*). The synovial membrane plays a central role in the inflammatory processes in rheumatoid arthritis and psoriatic arthritis, because misdirected immune cells migrate inward through it, or because the proliferation of fibroblasts on the synovial membrane can lead to the formation of a pannus, a cell clone of fibroblasts. Upon disintegration of the pannus, inflammation mediators such as interleukins and α-TNF (α-tumor necrosis factor) are secreted by the migrated immune cells. Via an inflammation cascade, these inflammation mediators control the release of proteases and other destructive enzymes from immune cells which then result in enzymatic destruction of the cartilaginous and bone structures. The following publications are mentioned by way of example in this connection:

"Analysis of the inflammatory cytokine network among TNF alpha, IL-1 beta, IL-1 receptor antagonist, and IL-8 in LPS-induced rabbit arthritis", Matsukawa A., Yoshimura T., Miyamoto K., Ohkawara S., Yoshinaga M., Lab Invest. 1997 May; 76(5):629-38. PMID: 9166282;

"Cytokine concentrations in the synovial fluid and plasma of rheumatoid arthritis patients: correlation with bony erosions", Fong K. Y., Boey M. L., Koh W. H., Feng P. H., Clin. Exp. Rheumatol. 1994 Jan.-Feb.; 12(1):55-8. PMID: 8162643;

"Study of pro-inflammatory (TNF-alpha, IL-1alpha, IL-6) and T-cell-derived (IL-2, IL-4) cytokines in plasma and synovial fluid of patients with juvenile chronic arthritis: correlations with clinical and laboratory parameters", Kutukculer N., Caglayan S., Aydogdu F., Clin. Rheumatol. 1998; 17(4):288-92. doi: 10.1007/BF01451007. PMID: 9776110;

"Preliminary report on cytokine determination in human synovial fluids: a consensus study of the European Workshop for Rheumatology Research", The Cytokine Consensus Study Group of the European Workshop for Rheumatology Research. Roux-Lombard P., Steiner G., Clin. Exp. Rheumatol. 1992 Sep.-Oct.; 10(5):515-20. PMID: 1333926 Review; and "The role of T-cell interleukin-17 in conducting destructive arthritis: lessons from animal models", Lubberts E., Koenders M. I., van den Berg W. B., Arthritis Res. Ther. 2005; 7(1):29-37. doi: 10.1186/ar1478. Epub 2004 Nov. 30. PMID: 15642151 Free PMC article. Review.

A range of active ingredient groups are available for the systemic drug therapy of rheumatoid arthritis and psoriatic arthritis. These active ingredient groups are subdivided into analgesics, nonsteroidal anti-inflammatory agents, glucocorticoids and basic therapeutic drugs (disease-modifying anti-rheumatic drugs, DMARD). In addition, there are modern antibodies (biologicals) which block the α-TNF (α-tumor necrosis factor) or the interleukin IL-17. Low molecular weight active ingredients which suppress the immune system are of particular interest. Important active ingredients of this kind are cyclosporin A (CAS 59865-13-3), tacrolimus (CAS 104987-11-3) and everolimus (CAS 159351-69-6).

The mechanism of action of cyclosporin A is attributable to the formation of a complex of cyclosporin A and the immunophilin cyclophilin. This complex inhibits the phosphatase calcineurin. The enzyme calcineurin is in turn essential for the formation of the α-TNF, wherein the α-TNF is a key compound at the start of the inflammation cascades. By inhibiting the synthesis of α-TNF it is accordingly also possible to inhibit the downstream inflammation cascades.

In systemic drug therapy, it is possible to achieve serum active ingredient concentrations for cyclosporin A in the range from approx. 75 µg/l to 175 µg/l and for tacrolimus from 5 µg/l to 20 µg/l. Higher systemic active ingredient concentrations are not possible for longer-term therapy due to the risk of unwanted systemic toxic side-effects for the rest of the body. This means that active ingredient concentrations are very low in the joint capsule tissue (*membrana fibrosa* and *membrana synovialis*) and can therefore have only a limited immunomodulating effect on the inflammatory process.

In order to reduce chronic inflammatory processes in the joint region of patients with rheumatoid arthritis and psoriatic arthritis, it would therefore be desirable if immunosuppressants could be administered directly to the joint capsule tissue in order to achieve a locally elevated concentration of these immunosuppressants.

Implants for delivering active pharmaceutical ingredients in the region of the joints which can be used for the local administration of antibiotics are already known. Documents GB 2 290 971 A, US 2010/0042213 A, WO 2017/178951 A1, WO 2007/084878 A1 and U.S. Pat. No. 6,245,111 B1 are mentioned by way of example in this connection. In these implants, however, a large area of the joint has already been removed and the implants are primarily used to treat the prostheses with antibiotics. Such implants cannot be considered for treating rheumatoid arthritis or psoriatic arthritis because the joint to be treated would have to be removed for the therapy and subsequent treatment would thus make no sense.

US 2007/0219471 A1 discloses an implant for administering active ingredients and maintaining reduced pressure in order to accelerate wound healing in and for mechanically stabilizing poorly healing cavities.

WO 2010/088548 A1 discloses a tubular, refillable eye implant with which an active pharmaceutical ingredient can be delivered directly to the eyeball. The tubular implant is to this end directly inserted into the eyeball. The implant is neither intended nor suitable for implantation in a joint. Insertion in the joint would attack and damage the joint itself and there would be a risk of infection and inflammation of the joint on insertion of the implant.

U.S. Pat. No. 5,681,289 A and US 2018/0028320 A1 disclose implants in which a medical liquid for treating joints or for lubricating joints is supplied to the joints from a reservoir via tubes. The implants are relatively large and can be set in place only with difficulty. Modifying a medical treatment at short notice is complicated because the supply lines to the two-dimensional applicators would first have to be flushed, which is not straightforwardly possible in the implanted state. The implants are well suited to lubricating joints with a lubricant delivered via the implant, whereas targeted delivery of active pharmaceutical ingredients at a high concentration with the assistance of these implants would not appear to be possible because the implant, the reservoir and the supply line contain excessively large volumes.

US 2003/0139811 A1 discloses an active ingredient system for local release of antiinflammatory active ingredients in the interior of joint capsules. This involves hollow screws with an orifice in the screw head. These hollow screws can be filled with an active ingredient. The screws are then introduced into bone tissue which, in addition to the cartilaginous tissue, is located within the joint capsule. The active ingredient is then intended to be released into the synovial fluid via the orifice in the screw head. Drawbacks here are that the joint capsule must be opened up and that the screw remains in the interior of the joint capsule once active ingredient release is complete. Opening up the joint capsule always involves a distinct risk of infection. Filling the implanted screw with new active ingredient is not provided. The treatment therefore also cannot be adapted to any change in the state of the treated patient.

The object of the invention is to overcome the disadvantages of the prior art. In particular, the intention is to provide an implant for local release of active ingredients with which local treatment with a high concentration of immunosuppressants is possible even over extended periods of time. The treatment should, if possible even at short notice, be adaptable to the patient's individual treatment situation.

The object of the invention is thus also to develop a subcutaneous implant which is suitable for local active ingredient release. It should preferably be possible for a medical user straightforwardly to resupply the implant located in the patient with fresh and different active ingredients without the implant having to be explanted for this purpose. It must be ensured that, when using the implant, the medical user cannot damage or injure the tissue structures to be treated with the implant. It should be possible to visualize the implant in the patient by X-ray imaging.

The objects of the invention are achieved by an implant for local active ingredient release, the implant having an upper wall, wherein the upper wall is closed and disk-shaped and consists of a material which is pierceable with a medical injection cannula using a force of less than 100 N, is self-sealing and is elastically deformable, a lower wall, wherein the lower wall is arranged opposite the upper wall, is disk-shaped, is elastically deformable and the lower wall has at least one feed-through through the lower wall, wherein the at least one feed-through is liquid-permeable, a hollow space which is arranged between the upper wall and the lower wall, and an anti-piercing means, wherein the anti-piercing means is arranged between the upper wall and the lower wall and is disk-shaped, wherein the anti-piercing means consists of a material which is not pierceable with a medical injection cannula using a force of less than 100 N.

The implant is preferably a medical implant. All the materials of the implant which can come into contact with the body or tissue of the body should therefore particularly preferably be biocompatible. The materials of which the upper wall and the lower wall consist are thus preferably biocompatible.

The implant is preferably intended to be implanted in the region of the outside of joint capsules in the case of chronic joint inflammation caused by autoimmune processes and is then accordingly provided and suitable for this purpose. Examples from the rheumatic group of diseases are chronic rheumatoid arthritis and psoriatic arthritis. The implant is thus particularly preferably an implant for treating chronic rheumatoid arthritis and psoriatic arthritis.

A medical injection cannula is taken to mean an injection cannula of any desired conventional commercial syringe from the medical field and not a special tool for piercing particularly hard materials. Such injection cannulas may for example be characterized by standards ISO 7864:2016 (2016-08) and DIN 13097-4 (1 Jun. 2019). Sterican® standard cannulas from B. Braun Melsungen AG are one example.

Self-sealing means that the upper wall, once it has been pierced by a medical injection cannula and the medical injection cannula has been withdrawn again from the upper wall, automatically closes back up in liquid-tight manner.

Provision may preferably be made for the implant to be flat and/or disk-shaped.

A disk-shaped body has a thickness or gage which is smaller than its width and depth and has a substantially planar shape.

The implant can be filled or loaded with a liquid and thus with at least one active ingredient both before and after implantation. The implant can then deliver the liquid or the at least one active ingredient through the at least one feed-through.

The implant may preferably be suitable and intended for local release of immunosuppressants. Once implanted, the implant can be reloaded multiple times with active ingredients by a medical user without the implant having to be explanted for this purpose.

Provision may be made for the implant and/or the upper wall and/or the lower wall to have a circular shape. In the case of a flat structure, this geometry provides the best volume to surface area ratio and can be readily implanted in joints.

Provision may be made for the upper wall and the lower wall to be connected together via a circumferential rim or to be connected together via a circumferential boundary of the anti-piercing means, wherein the upper wall and the lower wall are preferably connected together in liquid-tight manner.

In this way, a compact and flat structure of the implant is obtained, such that the latter can readily be superimposed on the outside of a joint capsule by implantation. If the upper wall and the lower wall are connected together in liquid-tight manner, the liquid can only be delivered from the hollow space through the at least one feed-through from the implant. The upper wall and the lower wall are preferably directly connected together via a circumferential rim of the upper wall and a circumferential rim of the lower wall. The circumferential rim may thus be part of the upper wall and/or the lower wall, in particular thus also be in two parts and be part both of the upper wall and of the lower wall. Provision may also be made for the upper wall and the lower wall to be connected together, in particular to be connected together in liquid-tight manner, by a latch mechanism.

Alternatively, the upper wall and the lower wall may, however, also be of one-part construction. This has advantages in particular in the production of very small implants. Production may for example proceed by placing the anti-piercing means in an elastic or rubber-elastic bladder and then shaping the lower wall and the upper wall by a blow molding method. The basic shape, into which the anti-piercing means is placed, may to this end be inflated with a gas pressure and pressed against an external shape and then solidified in this state.

Provision may moreover be made for the anti-piercing means to consist of metal or to consist to an extent of at least 50% of metal.

In this way, piercing of the anti-piercing means can be reliably prevented. In addition, metals can be particularly readily used in the medical field since there are many biocompatible metals and metal alloys. As a result, the anti-piercing means can furthermore be effectively visualized with X-rays. The position of the implant in the patient can thus easily be checked. Stainless steel, titanium, titanium alloys, tantalum, tantalum alloys and also silver-containing alloy as well as silver may preferably be considered as the metal.

Provision may further be made for the anti-piercing means to be arranged in the hollow space, wherein the anti-piercing means is preferably not firmly connected to the upper wall and the anti-piercing means is particularly preferably arranged on a side of the lower wall which faces the upper wall.

In this way, the anti-piercing means can lift away from the upper wall during injection of liquid into the hollow space and so extend the hollow space in this region. As a result, it can be ensured that, even in the case of a flat structure of the anti-piercing means, the orifice of the medical injection cannula is arranged in the interior of the hollow space above the anti-piercing means and as a result the liquid can be injected into the interior of the hollow space.

Provision may also be made for the lower wall to be pierceable with a medical injection cannula, wherein the lower wall preferably consists of a rubber-elastic plastics material.

In this way, the lower wall may be fabricated from a highly elastic material such as rubber, such that the hollow space is also extensible in the lower region. As a result, a larger quantity of the liquid can be injected into the hollow space. In this way, the lower side of the implant, i.e. the lower wall, can additionally adapt itself to the shape of the outer surface of the joint capsule.

According to a preferred further development, provision may be made for the hollow space to be elastically expandable by injection of a liquid, wherein the liquid in the expanded hollow space is preferably expellable with an elastic force from the hollow space through the at least one feed-through.

In this way, the liquid can be expelled into the surroundings from the hollow space by a pressure on the hollow space, in particular by the elastic restoring force acting on the upper wall and the lower wall.

Provision may moreover be made for the lower wall to have, on a side opposite the upper wall, protruding patterning which is suitable for distributing a liquid on this outer surface, wherein the protruding patterning is preferably ribs and/or bumps, and/or for the at least one feed-through to open into at least one channel on this outer surface of the lower wall and the at least one channel to be formed by the protruding patterning.

In this way, it is possible to prevent the at least one feed-through from being clogged or closed by a substrate. It is additionally ensured in this manner that the liquid from the hollow space can be effectively distributed on the outer surface of the lower wall. The implant is overlaid by soft tissue. This may exert pressure on the upper wall, wherein the upper wall can as a result exert pressure on the active ingredient solution in the hollow space. As a result, it is possible to accelerate the rate at which the active ingredient solution exits through the feed-through in the lower wall. The protruding patterning or the ribs and/or bumps on the lower side of the upper wall prevents movement of the upper wall in the direction of the lower wall. As a result, the pressure in the interior and the hollow space is relieved and expulsion of the active ingredient solution from the hollow space is prevented.

Provision may also preferably be made for the ratio of width to height and of depth to height of the implant to be at least 2:1 and preferably at least 3:1.

In this way, the implant can readily be implanted under the skin in the region of joints. In addition, the upper wall can very easily be located with a medical injection cannula in order to fill the hollow space or interior with a liquid.

Provision may also be made for a liquid to be present in the hollow space, wherein the liquid preferably contains at least one active pharmaceutical ingredient, wherein one of the at least one active ingredients is particularly preferably cyclosporin A, or an active ingredient solution or an active ingredient in the solid or semisolid state is present in the hollow space.

In this manner, the implant is directly usable for medical treatment or for delivery of a liquid or, after filling with a carrier liquid or a solvent for the solid or semisolid active ingredients, is usable for medical treatment or for delivery of a liquid.

Provision may further be made for the anti-piercing means to be at least as large as 50% of an interior surface of the lower wall which delimits the hollow space and is preferably at least as large as 75% of the interior surface of the lower wall.

In this way it is ensured that there is no need for the medical injection cannula to be placed or targeted with particular accuracy in order to avoid piercing the lower wall.

Provision may moreover be made for the anti-piercing means not to rest flush at a circumferential boundary of the anti-piercing means against the internal side of the hollow space.

As a result, the liquid in the hollow space can flow from the upper interior between the anti-piercing means and the upper wall to the lower interior between the anti-piercing means and the lower wall.

Provision may preferably be made for the implant to be disk-shaped and the upper wall to form an upper side of the implant and the lower wall to form a lower side of the implant, wherein the entire surface of the implant or the entire surface of the implant apart from a circumferential rim is preferably formed by the upper wall and the lower wall.

In this way, a compact and flat implant can be provided which is easy to locate with a medical injection cannula of a syringe such that the liquid is easily injectable into the hollow space.

According to a preferred further development, provision may be made for the hollow space to have an interior which is delimited by the upper part and by the anti-piercing means, wherein the interior preferably spaces the upper part from the anti-piercing means by at least 0.5 mm and particularly preferably by at least 1 mm.

In this way, it is ensured that an orifice in a medical injection cannula is arranged in the interior when a medical injection cannula is inserted through the upper part. As a result, it can be ensured that a medical liquid can be injected with the medical injection cannula into the interior and thus into the hollow space of the medical implant.

Provision may also be made for a pressure relief valve to be arranged in each of the at least one feed-throughs, which pressure relief valve opens to the outside from a minimum pressure and preferably opens to the outside from a minimum pressure of at least 20 kPa.

In this way, the liquid from the hollow space, and thus the active ingredients in the liquid, can be administered or released in targeted manner by pressure on the hollow space in the patient's body. In addition, backflow of body fluids into the implant can be prevented.

Provision may further be made for the upper wall and/or the lower wall to consist of a rubber-elastic plastics material or, apart from a rim, to consist of a rubber-elastic plastics material, wherein, after piercing by and withdrawal of a medical injection cannula, the rubber-elastic plastics material of the upper wall preferably contracts again and closes liquid-impermeably.

In this way, it is possible on the one hand to ensure that the liquid does not exit from the upper wall, and on the other hand the elastic force of the rubber-elastic plastics material can expel the liquid from the hollow space of the implant through the at least one feed-through.

Provision may preferably also be made for the upper wall and the lower wall to be fluid-tight and particularly preferably also to be active ingredient-tight, i.e. for an active ingredient present in the liquid to be incapable of diffusing through the upper wall and the lower wall.

Provision may preferably be made for the lower wall to consist of a rubber-elastic plastics material or at least in a central region to consist of a rubber-elastic plastics material which is pierceable with injection cannulas, wherein, after removal of the injection cannula, the orifice created by piercing is particularly preferably reclosable by the restoring force of the rubber-elastic plastics material.

Provision may moreover be made for the anti-piercing means to have at least one liquid-permeable opening, wherein the at least one opening preferably has a free cross-section of a maximum of 0.5 mm and particularly preferably of a maximum of 0.25 mm.

In this way, the liquid in the hollow space can flow from one side of the anti-piercing means to the other side of the anti-piercing means or arrive at the at least one feed-through of the lower wall.

Provision may moreover also be made for the anti-piercing means to have surface patterning on the side facing the lower wall and preferably to have surface patterning on the side facing the upper wall and on the side facing the lower wall.

This ensures that the lower wall does not lie too closely against the lower side which faces toward it of the anti-piercing means. Thanks to the surface patterning on the upper side of the anti-piercing means, it is possible to ensure that the orifice at the tip of the medical injection cannula is in any event arranged in the hollow space when the medical injection cannula is inserted through the upper wall as far as the anti-piercing means. The surface patterning may preferably be formed by grooves or also by circular indentations. Patterning arranged on the upper side of the anti-piercing means also prevent the medical injection cannula from slipping on the upper side of the anti-piercing means. It is alternatively also possible to provide the anti-piercing means with a circumferential boundary on the upper side thereof. The circumferential boundary may be an upwardly protruding rim. It is then also not possible for the medical injection cannula to slip, which could result in a second perforation of the upper wall. Provision may preferably further be made for the anti-piercing means to be shaped as a slightly concave disk. As a result, slippage of the medical injection cannula is likewise counteracted. Patterning on the lower side of the anti-piercing means may make it possible for the active ingredient solution to reach the at least one opening of the lower wall.

Provision may preferably be made for the anti-piercing means to be firmly connected to the lower wall.

In this way, the anti-piercing means can be fixed relative to the lower wall which it is intended to protect.

Provision may likewise be made for the anti-piercing means to have a concave shape and/or a protruding boundary on an upper side which faces the upper wall.

It is possible in this manner to prevent the tip of the medical injection cannula from slipping unintentionally. In addition, this also forms an interior in the concave depression and the upper wall, into which the liquid can be injected with the medical injection cannula.

Provision may further be made for the implant to have one or more lugs by which the implant can be sutured to soft tissue.

In this way, the implant can be fixed to soft tissue. In addition, this enables precise positioning of the implant and makes it possible to rule out any migration of the implant.

The objects underlying the present invention are also achieved by a method for filling such an implant having the steps of:

A) provision of the implant and a syringe filled with a liquid, wherein the syringe has a medical injection cannula, B) piercing of the upper wall with the medical injection cannula of the syringe, C) injection of liquid from the syringe through the medical injection cannula and into the hollow space of the implant, D) spreading of the liquid in the hollow space, wherein the liquid flows up to the at least one feed-through, and, E) optionally, elastic expansion of the hollow space by injection of the liquid.

The liquid preferably contains at least one active pharmaceutical ingredient. According to the invention, step E) is preferred but optional.

Provision may be made for the method not to involve any medical treatment of a human or animal body and/or for the liquid not to be delivered to a human or animal body in the context of the method.

It is hereby clarified that the method according to the invention is not a method for treating the human body.

Provision may moreover be made in step B) for the tip of the medical injection cannula to be inserted through the upper wall to such an extent that it comes into contact with the anti-piercing means, wherein an orifice at the tip of the medical injection cannula is then located in an interior of the hollow space, wherein the interior of the hollow space is arranged between the anti-piercing means and the upper wall.

In this way, it is possible to ensure that the liquid can be injected into the hollow space with the medical injection cannula.

Provision may preferably be made for the following steps F) and G) and optionally H) to proceed after step E):

F) withdrawal of the medical injection cannula from the hollow space and the upper wall and G) liquid-tight closure of the upper wall by rubber-elastic recovery of the upper wall, and optionally H) compression of the hollow space due to the elastic restoring force of the elastically expanded hollow space and expulsion of the liquid from the hollow space through the at least one feed-through.

It is thus possible to ensure that the medical liquid is administered only through the at least one feed-through and does not unintentionally exit from the opposite, upper side of the implant.

The invention is based on the surprising recognition that, by way of the anti-piercing means in the middle between two elastic walls, it is possible to provide a compact implant which has a flat structure and is thus suitable for subcutaneous use in the region of joints, wherein the implant is pierceable in one wall with a medical injection cannula, such that the implant can straightforwardly repeatedly be filled through the skin, and the implant has on the opposing wall thereof at least one feed-through, through which the liquid containing the active ingredients or the active ingredients can be delivered at high concentration directly to the external joint capsule surface or to the site to be treated. Thanks to the elastically expandable hollow space, the liquid can be continuously delivered from the hollow space of the implant. Thanks to the disk-shaped lower wall which, implanted, lies on the joint as the substrate, it is possible to achieve extensive contacting and a fanned out distribution of the active ingredient on the joint. Due to the elastic conformability of the implant, the implant can be at least somewhat adapted to the shape of the surface of the joint to be treated. The anti-piercing means here prevents its being possible inadvertently to pierce the implant and so cause injury to the underlying tissue. In addition, it is possible to prevent the liquid from inadvertently not being administered within the implant. The implant according to the invention ensures that the implant located in the patient can be filled multiple times by a medical user with the assistance of conventional medical injection cannulas of ordinary syringes without the implant having to be explanted for this purpose. The anti-piercing means ensures that a medical user cannot perforate or damage the tissue structures under the implant with the medical injection cannulas.

The implant according to the invention preferably has the morphology of a slightly upwardly curved disk. The lower wall and the upper wall are preferably formed from a soft, rubber-elastic material. As a result, the implant can adapt itself to the surface morphology of the implantation site. The implant is preferably flat and, in plan view, particularly preferably circular or elliptical. It preferably has a diameter in the range from 3 mm to a maximum of 20 mm. Larger implants are particularly intended for local active ingredient release to the joint capsule of the knee joint. Implants with a small diameter can be implanted in the region of the finger joints and the basal joint of the hand. The at least one opening preferably has a diameter of less than 0.5 mm and particularly preferably of less than 0.25 mm. It is also possible to arrange two or more openings in the lower wall. It has been recognized in the context of the present invention that it is advantageous for the implant to be capable of providing delayed release of active pharmaceutical ingredients in the form of active ingredient solutions only on the side which faces the tissue to be treated.

The implant is preferably used in the manner such that the implant is firstly implanted subcutaneously onto the external surface of the joint capsule of the joint to be treated. It is possible to implant not only an implant which is already filled with active ingredient solution but also an as yet unfilled implant. Once the implant has been successfully positioned, it can be sutured for fixation to the surrounding soft tissue. If the implant was implanted in the state in which it is not filled with active ingredient, a medical user can supply it with any desired pharmaceutical active ingredient solutions, particularly preferably supply it with solutions of immunomodulators. The active ingredient solution to be administered is to this end drawn up in a syringe, wherein the syringe is connected to an injection cannula (hypodermic needle) with a diameter of less than 0.5 mm. The cannula is then inserted through the patient's skin in the direction of the implant and the upper wall perforated. The anti-piercing means then stops the injection cannula from penetrating any further. The active ingredient solution is then administered into the interior or hollow space. Once administration is complete, the injection cannula is withdrawn from the interior or hollow space and from the upper wall. The perforation in the upper wall closes up due to the restoring force of the rubber-elastic material of the upper wall. The active ingredient solution is released by diffusion from the at least one feed-through which is permeable to liquids on the lower side of the lower wall. It goes without saying that the implant can also be filled prior to implantation with an active ingredient or with a liquid containing at least one active ingredient with the assistance of the syringe.

Active pharmaceutical ingredients which may preferably be considered are immunomodulators which are sufficiently resistant to hydrolysis over an extended period. Preferred immunomodulators are cyclosporin A (CAS 59865-13-3), tacrolimus (CAS 104987-11-3) and everolimus (CAS 159351-69-6). Corticosteroids such as cortisone (CAS 53-06-5), betamethasone (CAS 378-44-9), triamcinolone (CAS 124-94-7), dexamethasone (CAS 50-02-2), dexamethasone phosphate (CAS 2392-39-4) may additionally be used as immunomodulators. The immunomodulator apremilast (CAS 608141-41-9) could moreover also be used. Particularly preferred immunomodulators are those which have very low solubility in water at room temperature.

Once the active ingredient has been released, the implant can be filled multiple times with active ingredient solution with the assistance of a syringe and an injection cannula, without explanation of the implant being necessary.

An exemplary implant according to the invention for local active ingredient release is composed of
  a) a disk-shaped base member as lower wall with at least one feed-through which liquid-permeably connects the upper side of the disk-shaped main body to the lower side of the disk-shaped main body,
  b) a disk which is not pierceable with injection cannulas as anti-piercing means which is placed on the disk-shaped base member,
  c) a liquid-impermeable cover as upper wall, wherein the liquid-impermeable cover is disk-shaped and elastically deformable and is connected to the disk-shaped base member, and
  d) an interior which is delimited by the internal side of the liquid-impermeable cover and the upper side of the disk which not pierceable with injection cannulas.

According to the invention, provision may be made for the liquid-impermeable cover to consist of a rubber-elastic plastics material or in a central region to include such a plastics material, wherein the liquid-impermeable cover is pierceable with injection cannulas, wherein, after removal of the injection cannula, the orifice created by piercing is reclosable by the restoring force of the rubber-elastic plastics material.

The liquid-impermeable cover may be liquid-impermeably connected at the entire circumferential rim to the disk-shaped base member. As a result, the active ingredient solution can only exit from the at least one feed-through of the disk-shaped main body.

It is advantageous for ribs and/or bumps to be arranged as spacers on the lower side of the liquid-impermeable cover. The implant is overlaid by soft tissue. This may exert pressure on the liquid-impermeable cover, wherein the liquid-impermeable cover can as a result exert pressure on the active ingredient solution in the hollow space. As a result, it is possible to accelerate the rate at which the active ingredient solution exits through the at least one feed-through in the disk-shaped main body. Ribs and/or bumps on the lower side of the liquid-impermeable cover prevent any movement of the liquid-impermeable cover in the direction of the disk-shaped main body. As a result, the pressure in the interior or the hollow space is relieved and expulsion of the active ingredient solution from the hollow space is prevented.

Another nine further exemplary embodiments of the invention and the course of a method according to the invention are explained below with reference to thirty three schematic figures but without thereby limiting the invention. In the figures.

In the figures and the following description of the nine exemplary embodiments of the present invention, i.e. of the nine implants according to the invention, explained with reference to the figures, some of the same reference signs are used for the same or similar parts in different exemplary embodiments or for different implants and for different individual parts of the implant so as to simplify comparability of the exemplary embodiments and readability.

Figure 1:
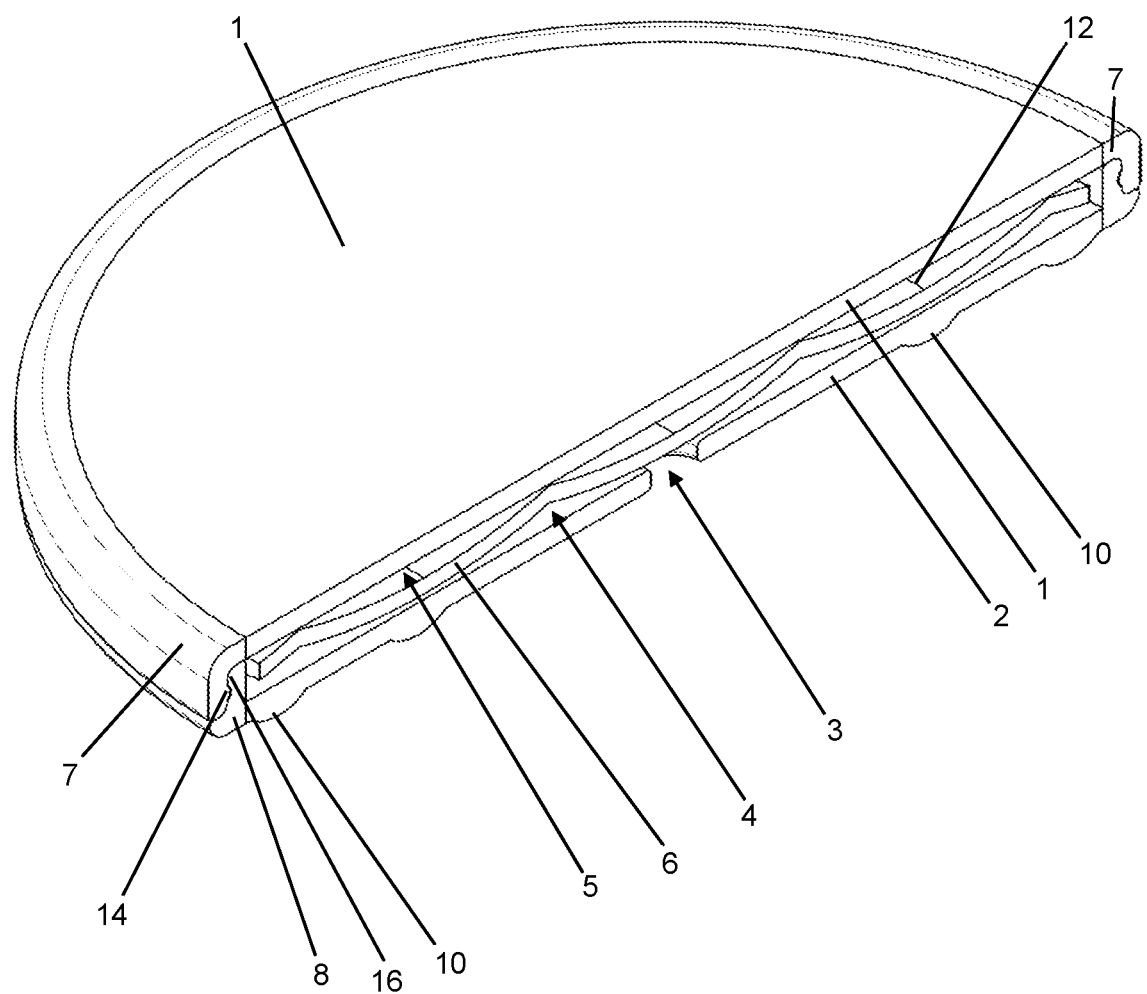
FIG. 1 is a schematic perspective cross-sectional view through a first exemplary implant according to the invention for the local administration of liquids.
Figure 2:
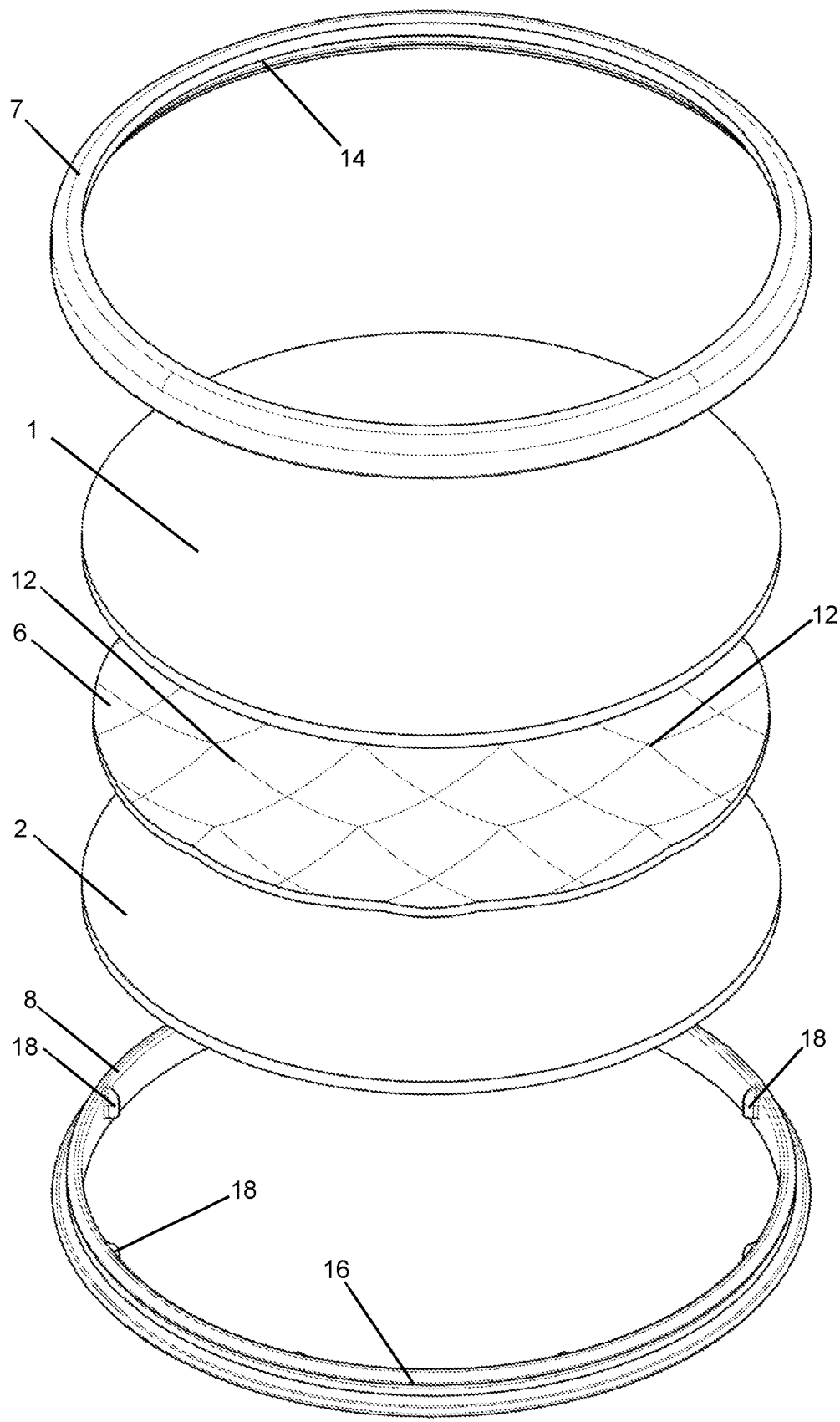
FIG. 2 is a schematic perspective exploded view of the first implant according to FIG. 1.
Figure 3:
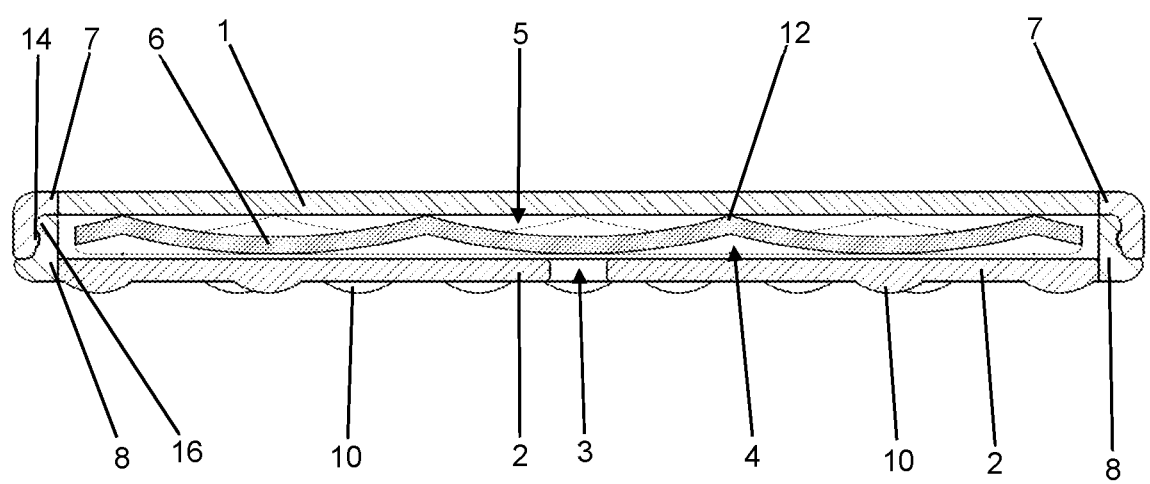
FIG. 3 is a schematic cross-sectional view of the first implant according to FIGS. 1 and 2.
Figure 4:
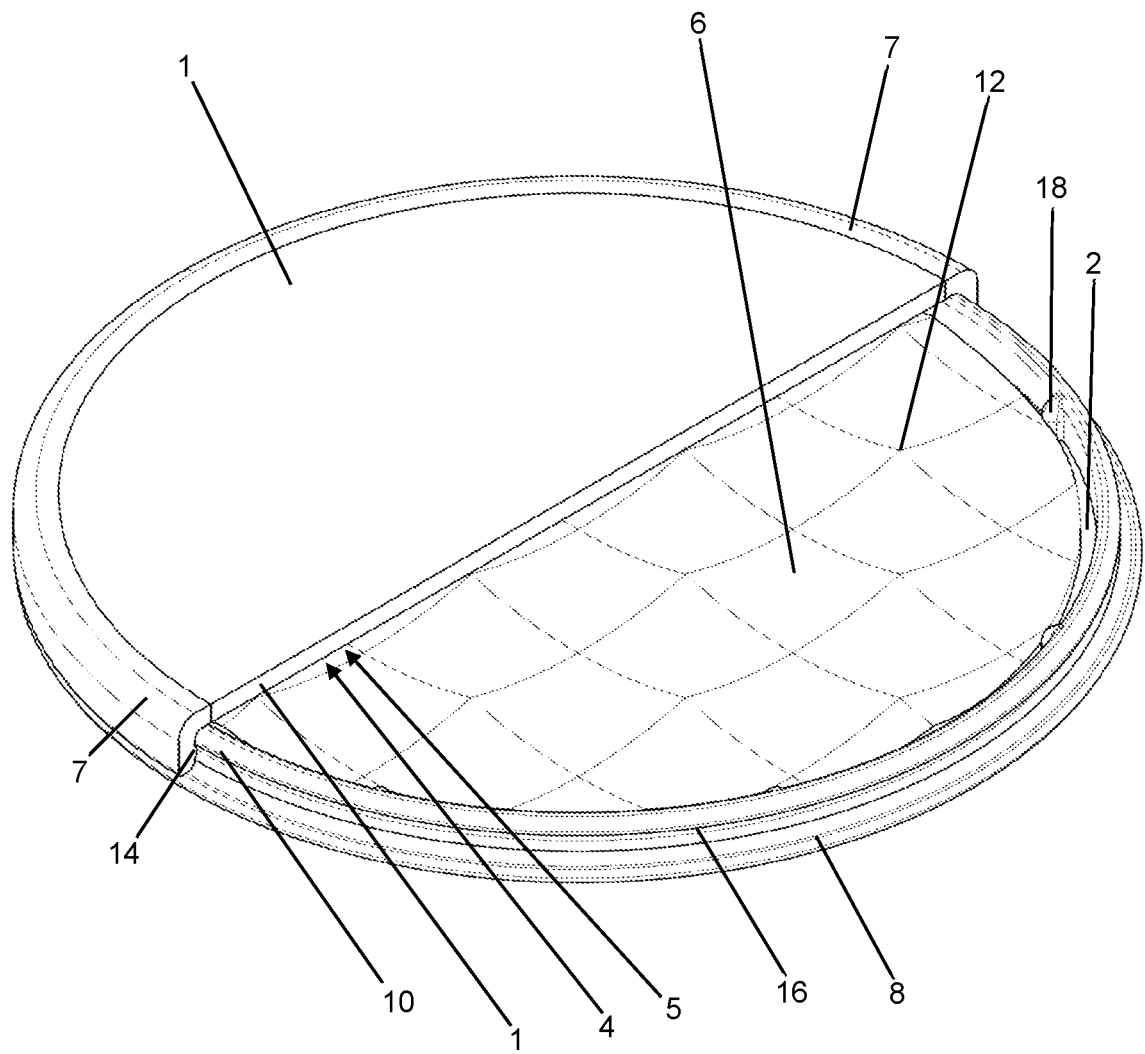
FIG. 4 is a schematic, perspective, partially sectional view onto the first implant according to FIGS. 1 to 3.
Figure 5:
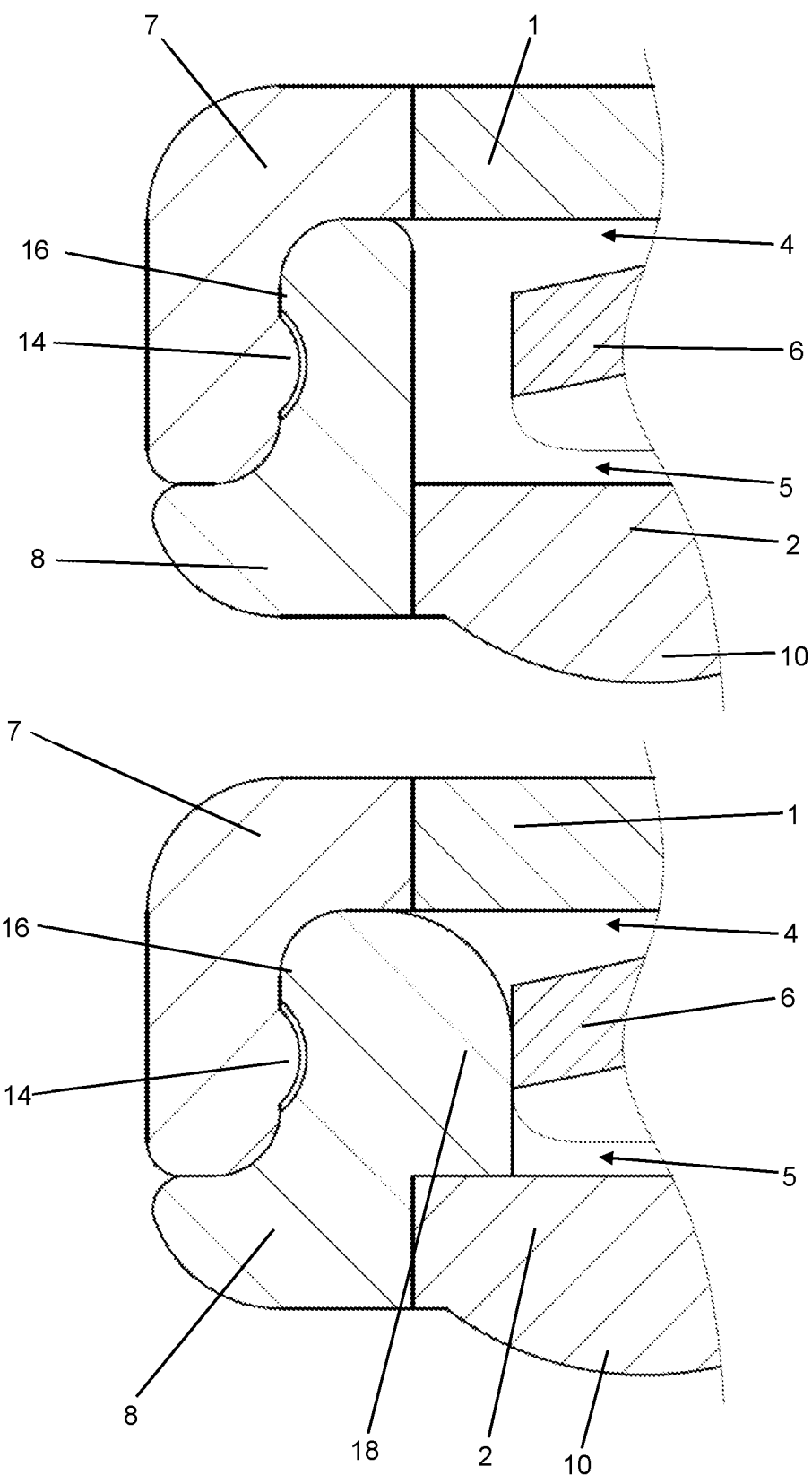
FIG. 5 shows two schematic cross-sectional views as enlarged details of the first implant according to FIGS. 1 to 4.
Figure 6:
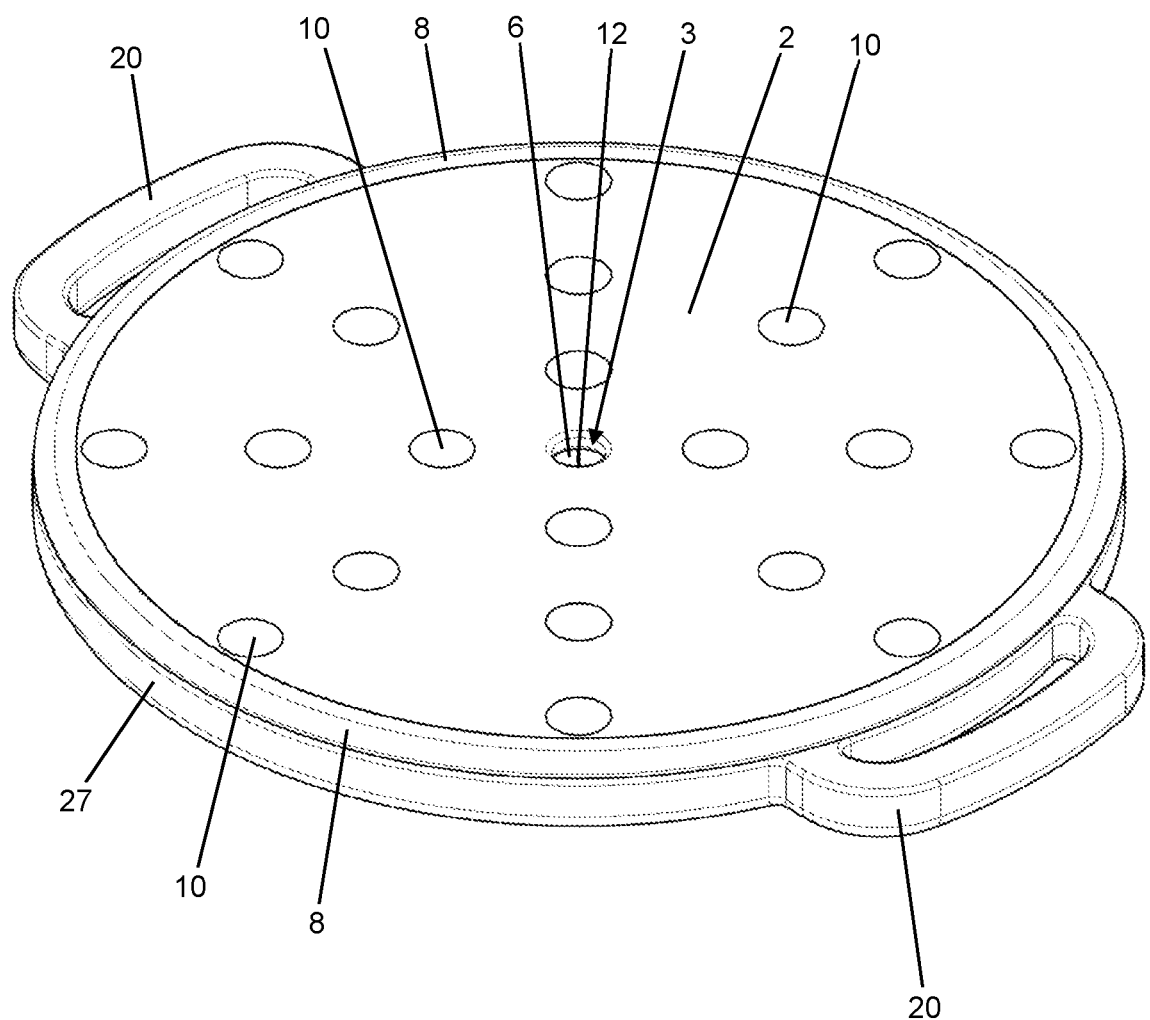
FIG. 6 is a schematic perspective plan view onto the lower side of a second exemplary implant for the local administration of liquids.
Figure 7:
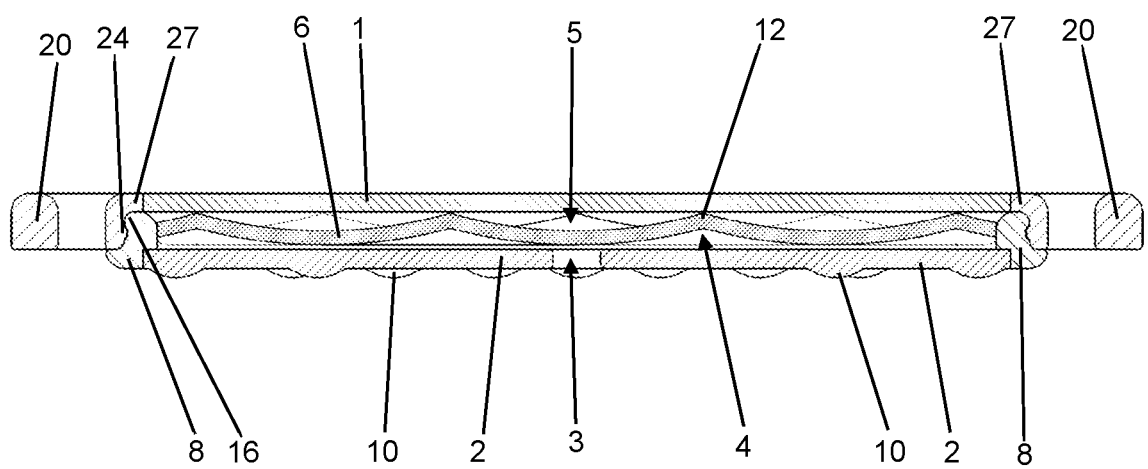
FIG. 7 is a schematic cross-sectional view of the second implant according to FIG. 6.
Figure 8:
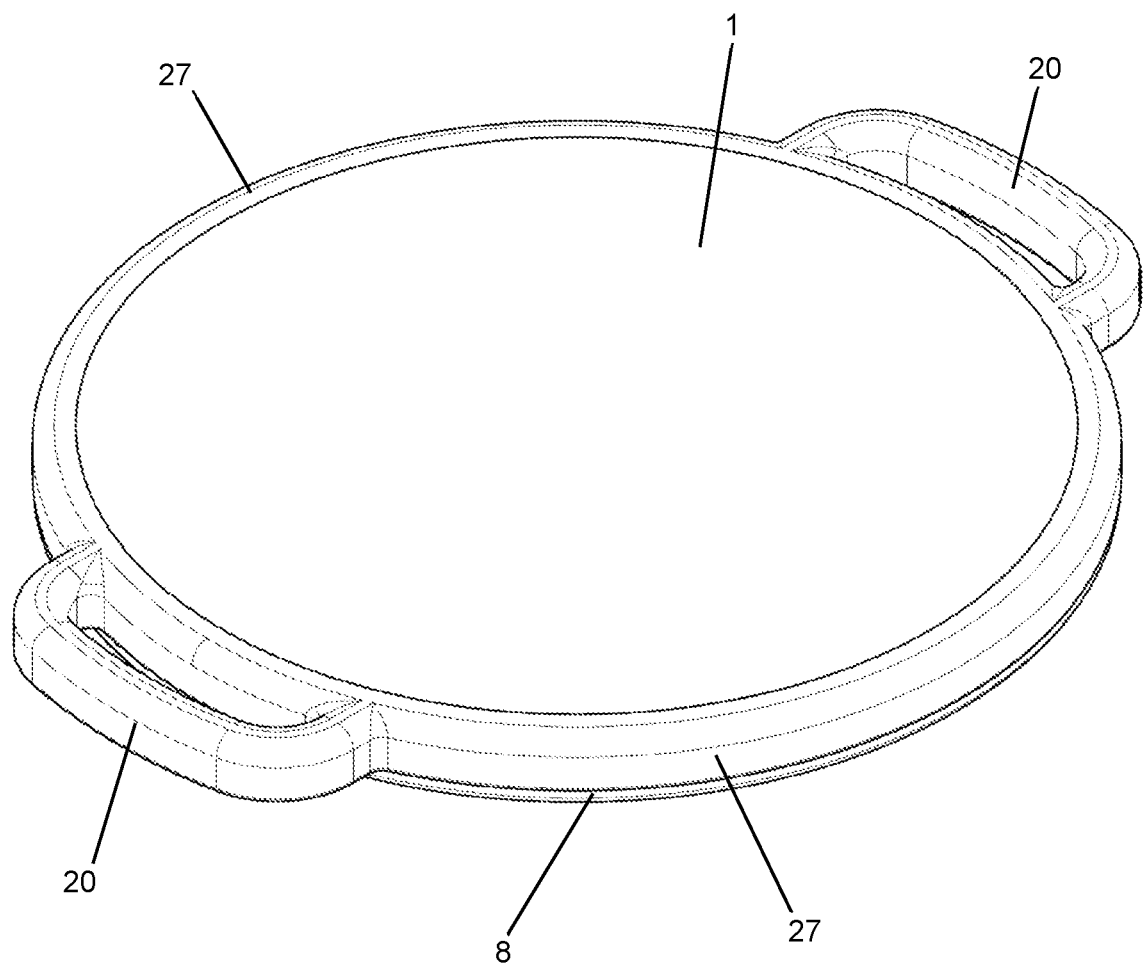
FIG. 8 is a schematic perspective plan view onto the upper side of the second exemplary implant according to FIGS. 6 and 7.
Figure 9:
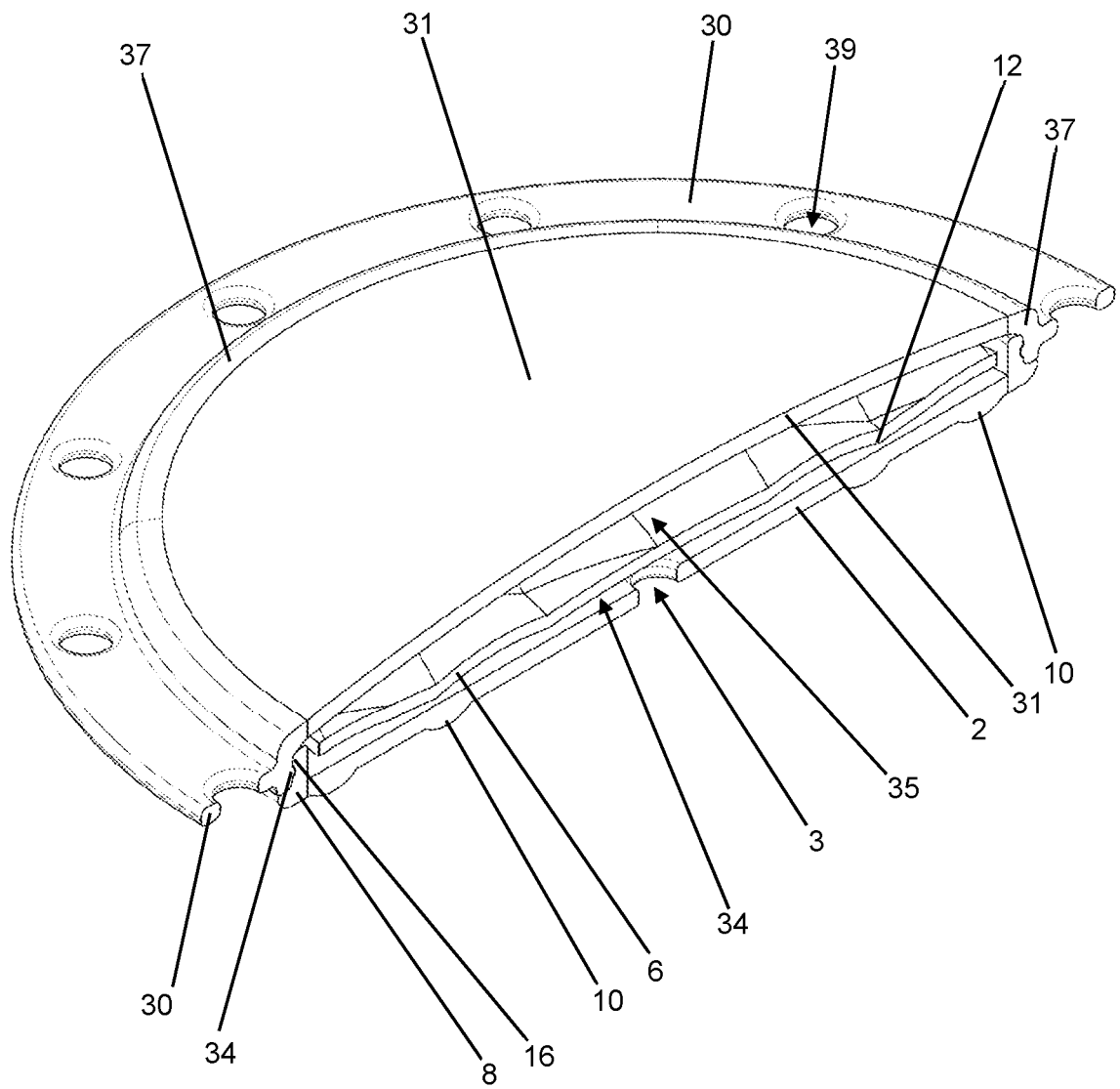
FIG. 9 is a schematic perspective cross-sectional view through a third exemplary implant for the local administration of liquids.
Figure 10:
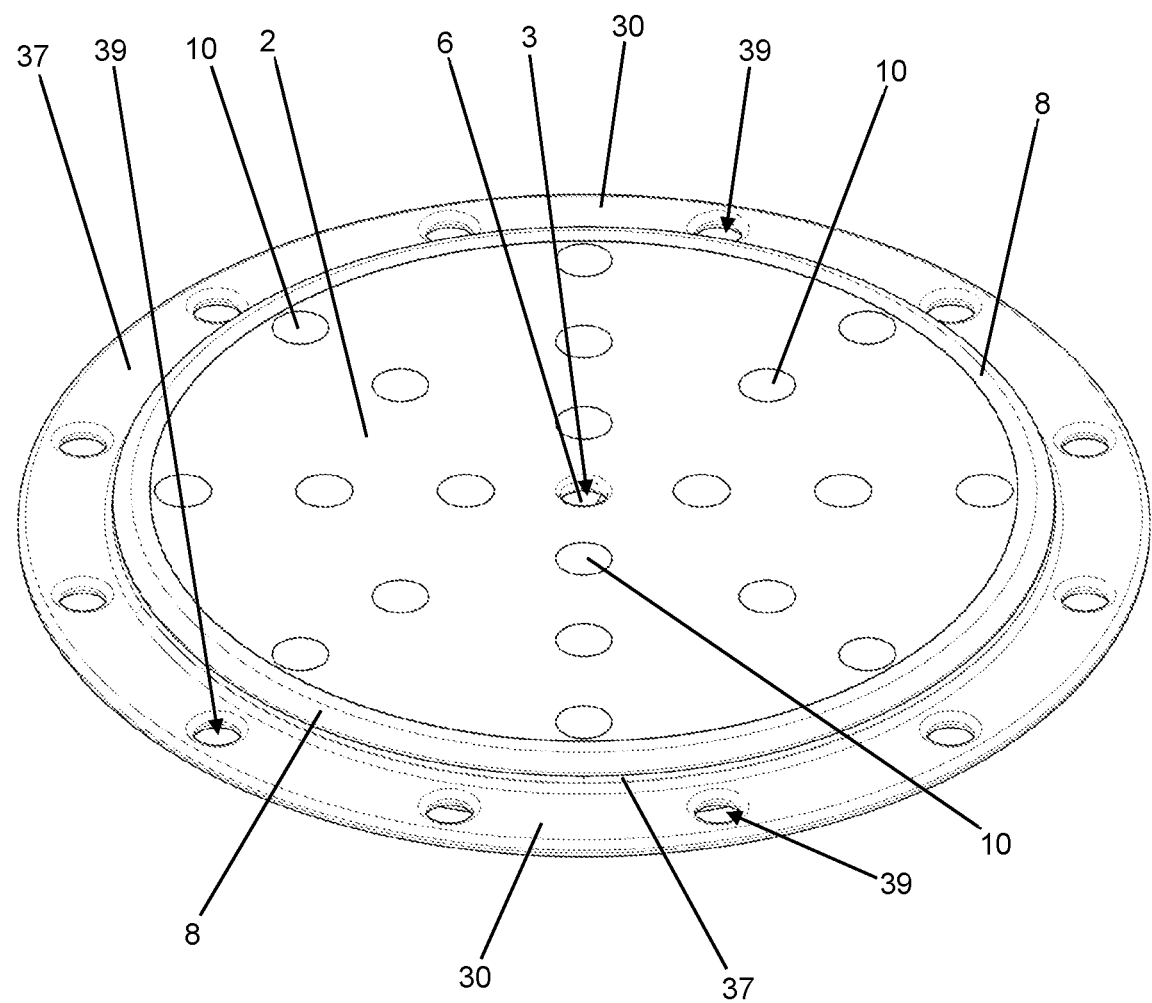
FIG. 10 is a schematic perspective plan view onto the lower side of the third implant according to FIG. 9.
Figure 11:
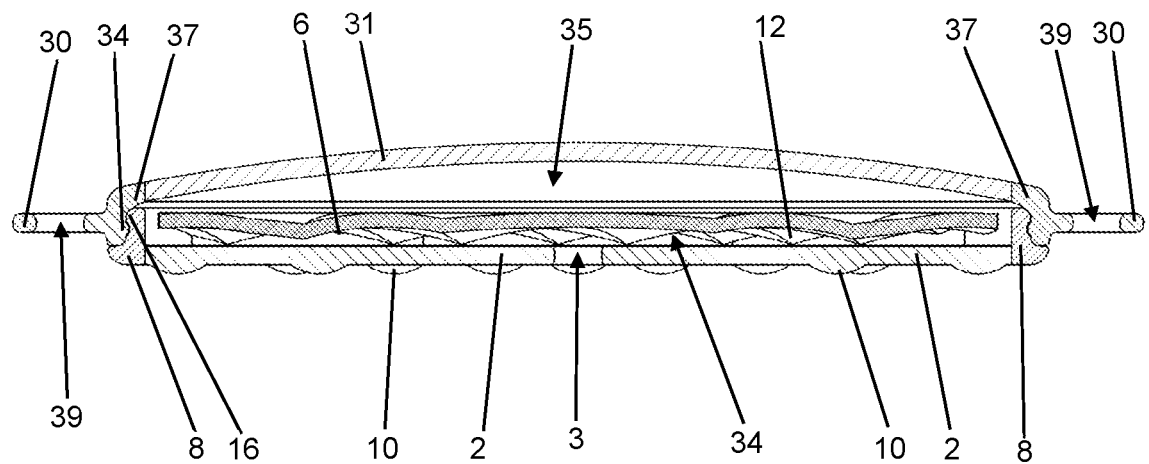
FIG. 11 is a schematic cross-sectional view through the third implant according to FIGS. 9 and 10.
Figure 20:
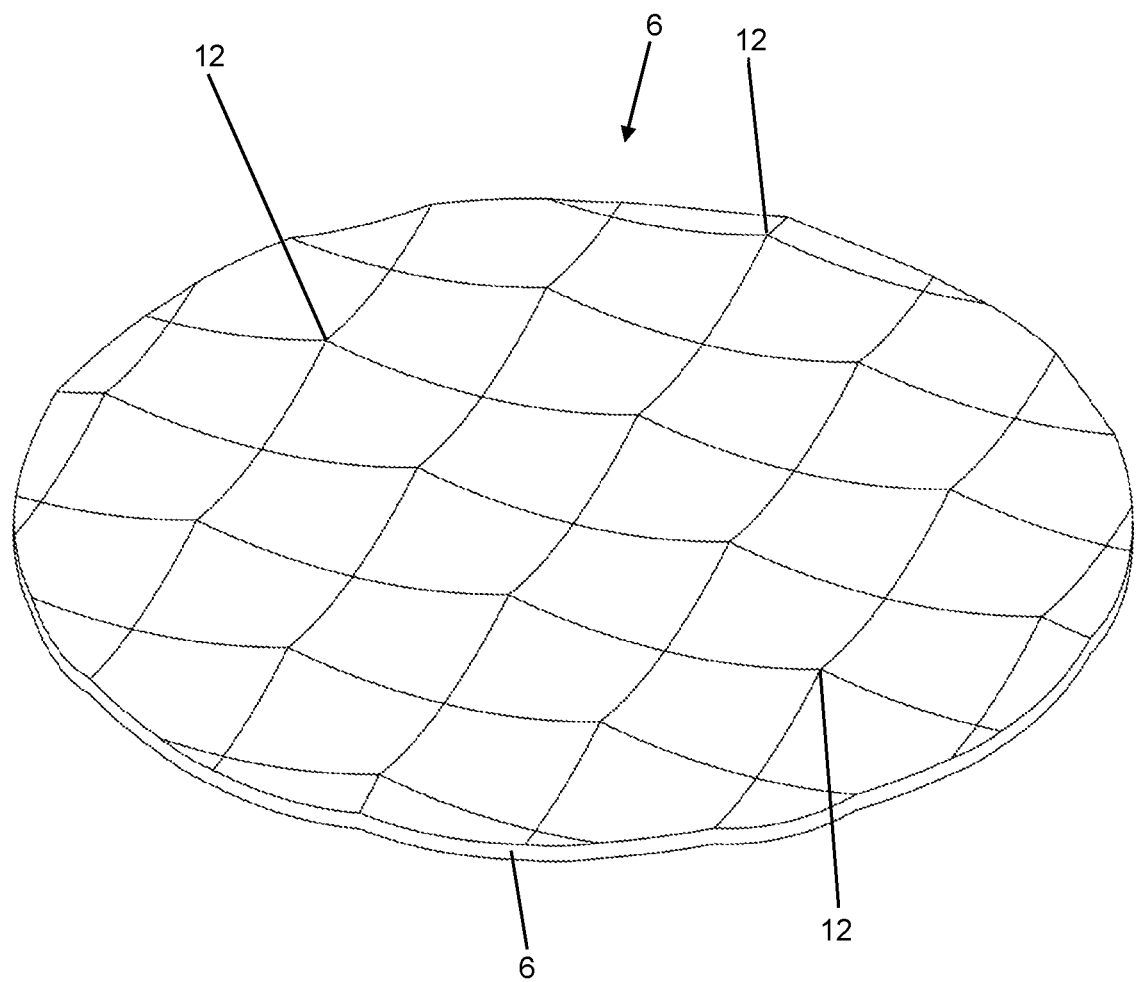
FIG. 20 is a schematic perspective plan view onto an anti-piercing means, as is present in the exemplary implants according to FIGS. 1 to 19.
Figure 21:
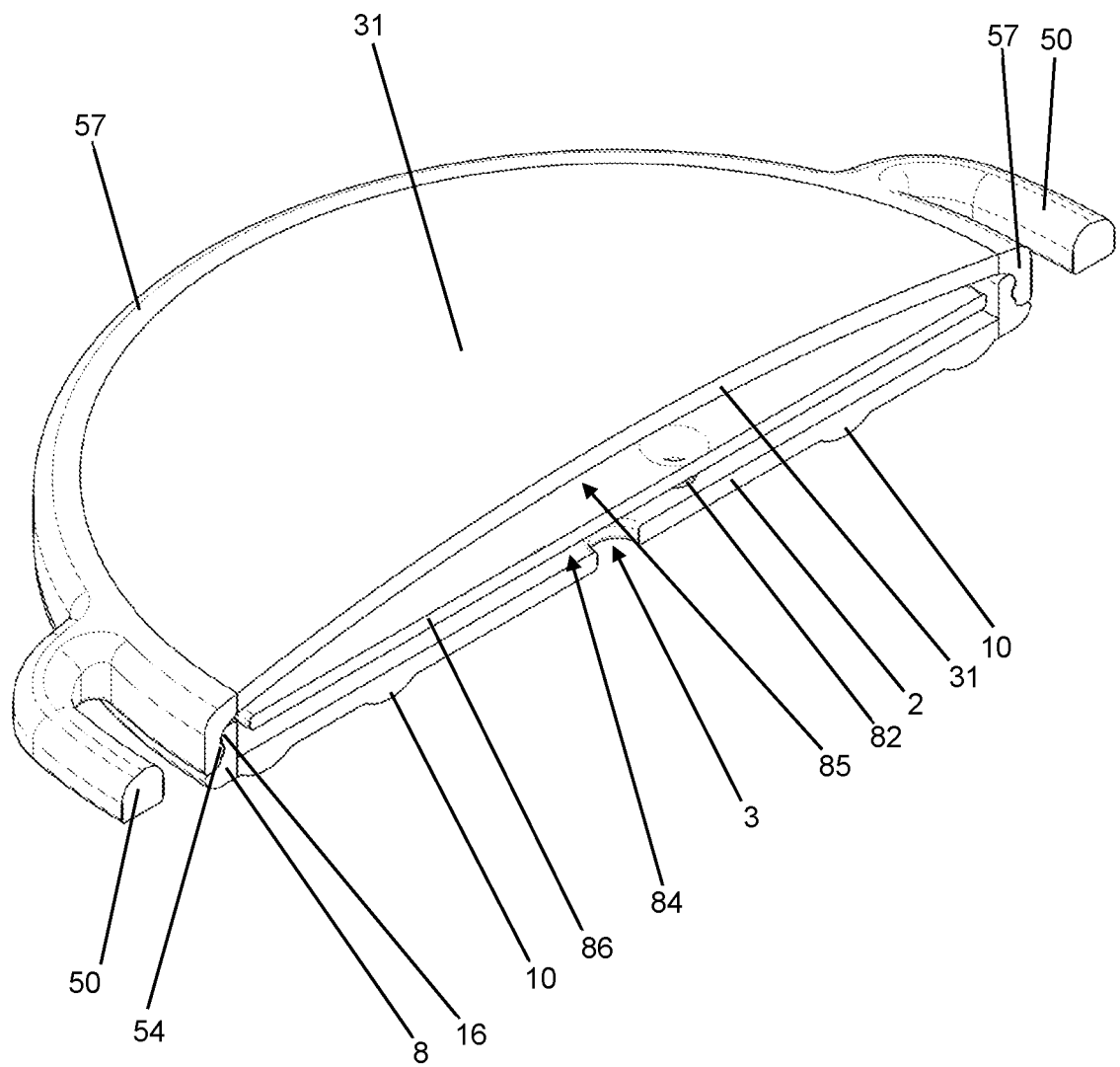
FIG. 21 is a schematic perspective cross-sectional view through an eighth exemplary implant for the local administration of liquids.
Figure 22:
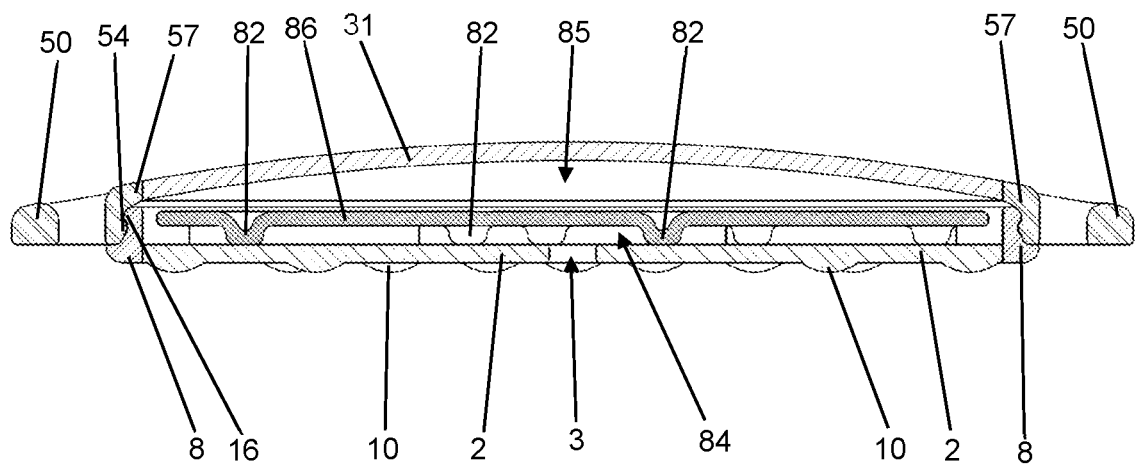
FIG. 22 is a schematic cross-sectional view of the eighth implant according to FIG. 21.
Figure 23:
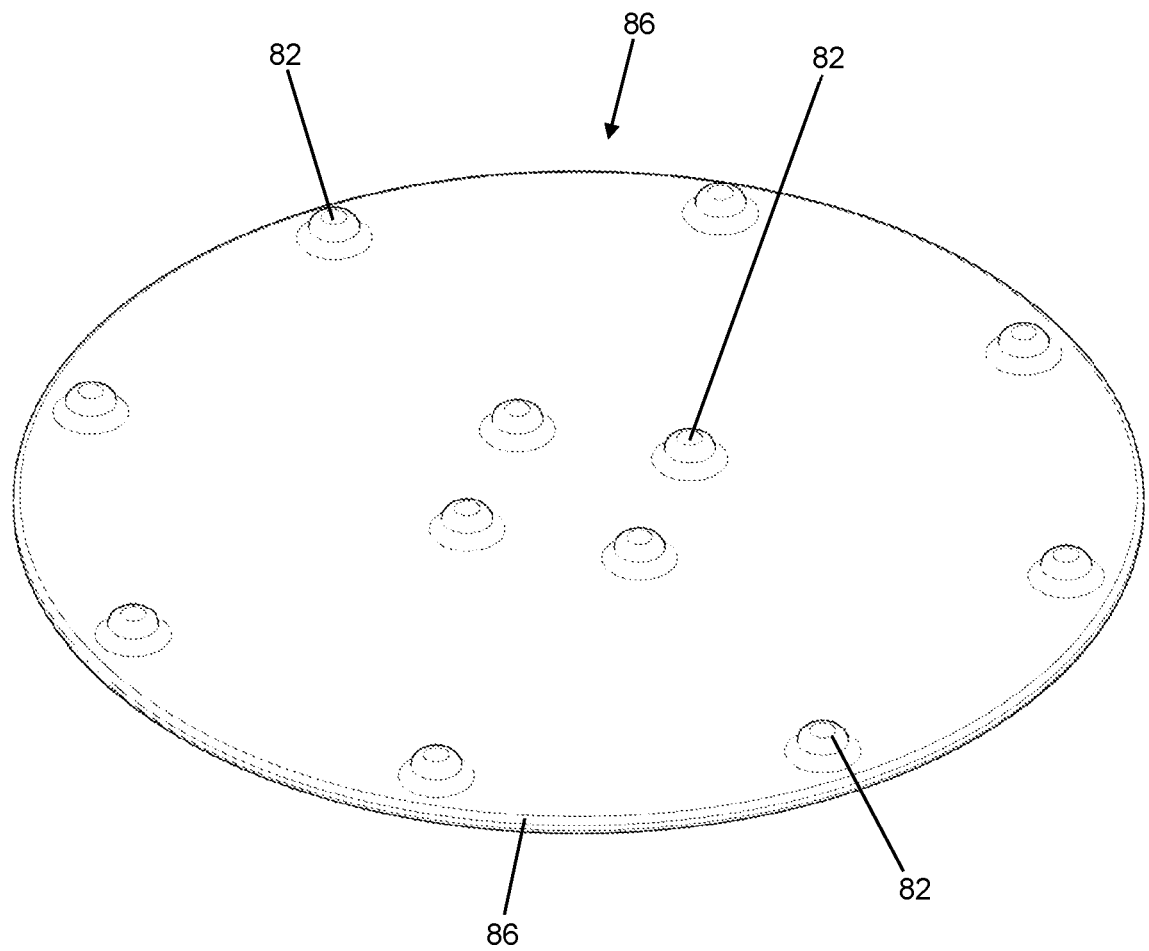
FIG. 23 is a schematic perspective plan view onto the lower side of an anti-piercing means of the eighth exemplary implant according to FIGS. 21 and 22.
Figure 24:
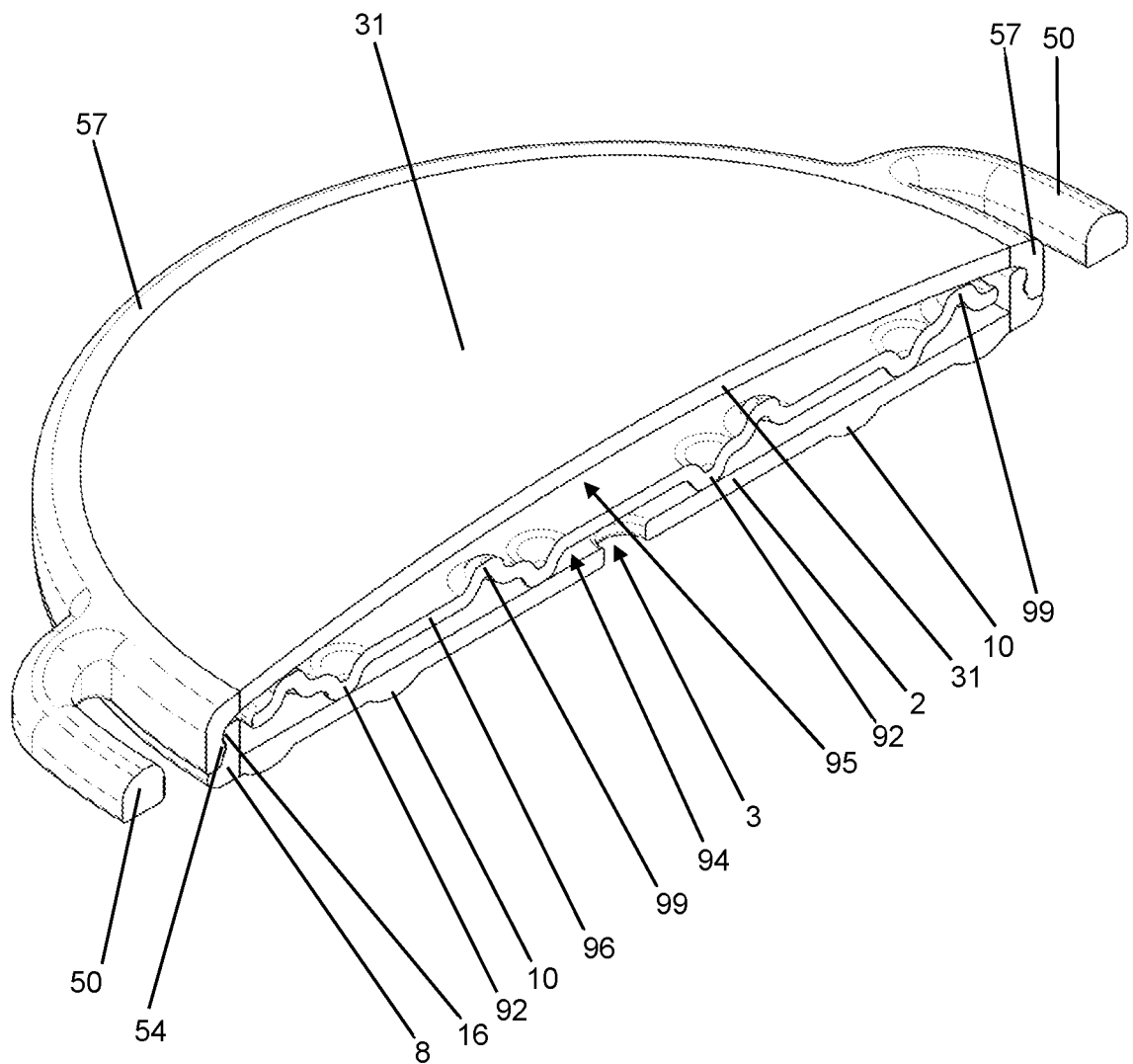
FIG. 24 is a schematic perspective cross-sectional view through a ninth exemplary implant for the local administration of liquids.
Figure 25:
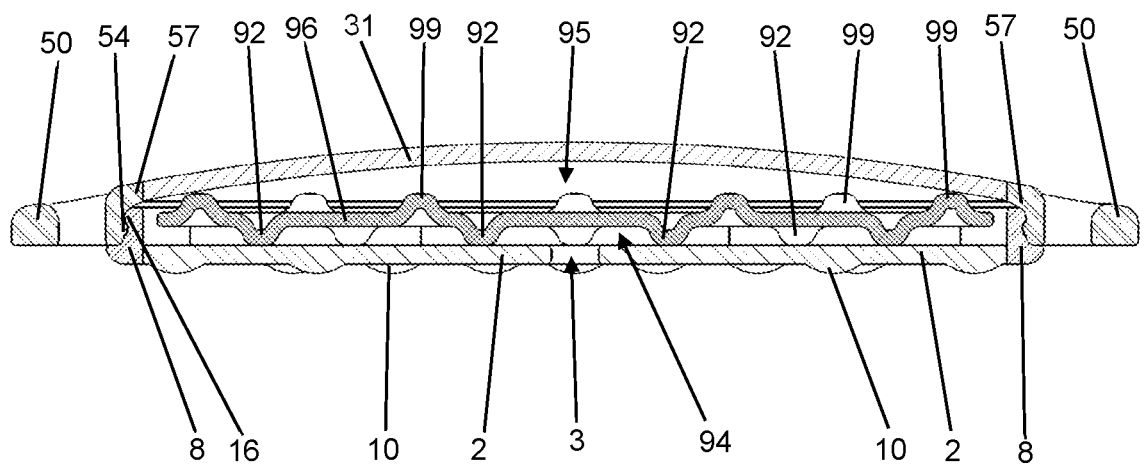
FIG. 25 is a schematic cross-sectional view of the ninth implant according to FIG. 24.
Figure 26:
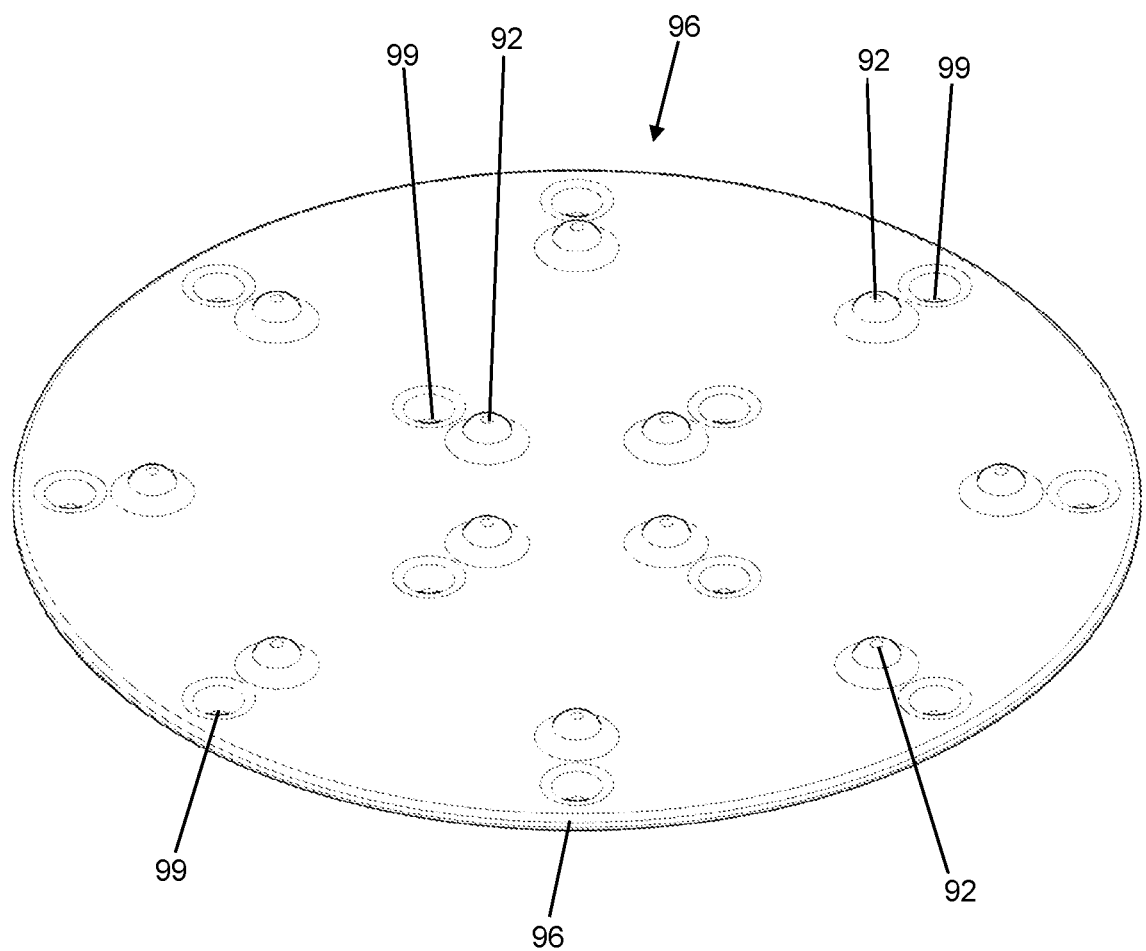
FIG. 26 is a schematic perspective plan view onto the lower side of an anti-piercing means of the ninth implant according to FIGS. 24 and 25.
Figure 27:
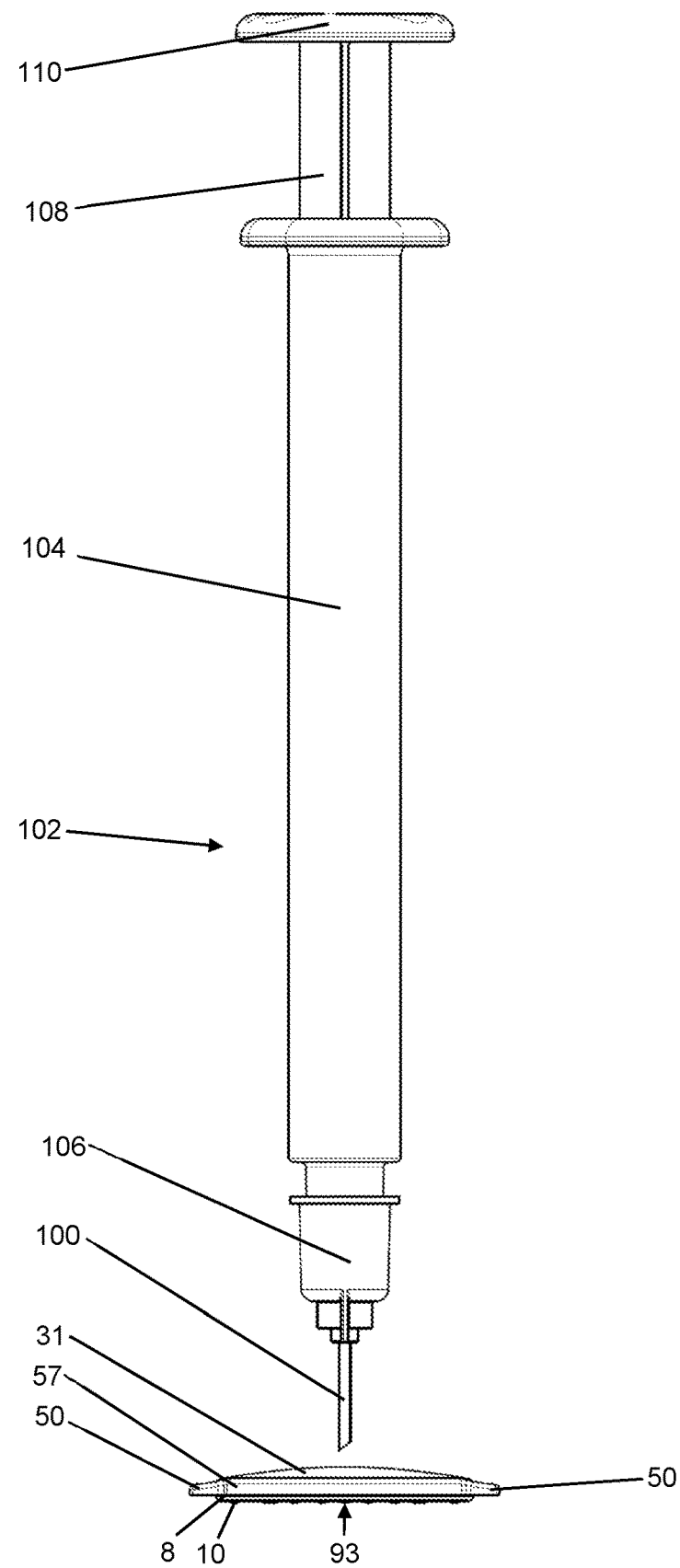
FIG. 27 is a schematic side view onto a syringe and the ninth implant before insertion of the injection cannula into the ninth implant.

FIGS. 1 to 5 show a first exemplary implant according to the invention for the local administration of a liquid in different representations. FIGS. 6 to 8 show a second exemplary implant according to the invention for the local administration of a liquid in different representations. FIGS. 9 to 11 show a third, FIGS. 12 and 13 a fourth, FIGS. 14 and 15 a fifth, FIGS. 16 and 17 a sixth and FIGS. 18 and 19 a seventh exemplary implant according to the invention for the local administration of a liquid in different representations. FIG. 20 shows an anti-piercing means as is used in the first seven exemplary embodiments. FIGS. 21 to 23 show an eighth exemplary implant according to the invention for the local administration of a liquid in different representations with another anti-piercing means. FIGS. 24 to 26 show a ninth exemplary implant according to the invention for the local administration of a liquid in different representations. FIGS. 27 to 33 show the course of a method according to the invention method for filling an implant with a syringe on the basis of the ninth exemplary implant, wherein the method is also straightforwardly transferable to the other exemplary embodiments.

The implant according to the first exemplary embodiment according to FIGS. 1 to 5 has an upper wall 1. The upper wall 1 is pierceable using manual force with a conventional medical injection cannula (as is shown for the ninth exemplary embodiment in FIGS. 27 to 33). The upper wall 1 may form an upper side of the implant. The material for the upper wall 1 may be such that, once an inserted injection cannula has been withdrawn, the upper wall 1 automatically closes back up. The upper wall may to this end consist of a rubber-elastic plastics material or rubber, or at least in a central region include a rubber-elastic plastics material or rubber. Such self-sealing membranes may for example be used in vials for drawing up syringes.

A lower wall 2 with a feed-through 3 is arranged on the lower side of the implant which is opposite the upper side, wherein a plurality of feed-throughs (not shown) may also be provided. The feed-through 3 may be arranged centrally in the middle of the lower wall 2. The feed-through 3 connects the upper side of the lower wall 2 to the lower side of the upper wall 1 and thus to the lower side of the implant.

The upper wall 1 and the lower wall 2 delimit a hollow space 4 in the interior of the implant. The feed-through 3 liquid-permeably connects the hollow space 4 of the implant to the surroundings of the implant. An interior 5, which is a portion of the hollow space 4, may be arranged between an anti-piercing means 6 in the hollow space 4 and the upper wall 1. The anti-piercing means 6 is disk-shaped and is arranged in the hollow space 4 between the lower wall 2 and the upper wall 1. The anti-piercing means 6 may be disk-shaped. The anti-piercing means 6 may have a smaller diameter than the hollow space 4, such that it divides the hollow space 4 into two parts in non-liquid-tight manner, or into two regions liquid-permeably connected together. FIG. 20 shows the anti-piercing means 6 in detail. The anti-piercing means 6 is not pierceable using manual force with a conventional medical injection cannula (as is shown for the ninth exemplary embodiment in FIGS. 27 to 33).

The upper wall 1 may have a circumferential upper rim 7. The upper rim 7 of the upper wall 1 may form a circle which encloses the upper wall 1. The lower wall 2 may have a circumferential lower rim 8. The lower rim 8 of the lower wall 2 may form a circle which encloses the lower wall 2.

The lower wall 2 may have on a lower side bumps 10 which protrude from the lower side of the lower wall 2. In this manner it is possible to ensure that, when the implant is lying with the lower side of the lower wall 2 on a support, it maintains a space there. Thanks to the resultant interspace, the liquid which exits through the feed-through 3 from the hollow space 4 can then be distributed along the surface of the lower wall 2.

The anti-piercing means 6 may have an undulating shape which forms protruding patterning 12 on the upper side and the lower side of the anti-piercing means 6 (see FIG. 20). In this way, it is possible to ensure that a lower side of the upper wall 1 is spaced from an upper side of the anti-piercing means 6 in such a manner that the tip of an injection cannula can penetrate into the interior 5 in order to inject the liquid therein. In addition, an upper side of the lower wall 2 can accordingly be spaced from the lower side of the anti-piercing means 6, such that a liquid can be spread without any problem in the lower part of the interior 4 and be spread up to the feed-through 3.

The upper wall 1 and the lower wall 2 may be connected together in liquid-tight manner via the upper rim 7 and the lower rim 8, such that, apart from the feed-through 3, the hollow space 4 is closed in liquid-tight manner. To this end, a latching ring 14 may be formed on the upper rim 7 and a latching ring 16 on the lower rim 8. The latching ring 14 of the upper rim 7 is capable of engaging in the latching ring 16 of the lower rim 8 when the upper wall 1 is pushed completely into place on the lower wall 2.

The use of such an implant and thus a method according to the invention may proceed by an injection cannula of a syringe being inserted through the upper wall 1 in a central region. A liquid can then be injected from the syringe into the interior 5. The anti-piercing means 6 may be held centrally with the assistance of tabs 18 projecting into the hollow space 4, such that the anti-piercing means 6 is laterally spaced from the lower rim 8 (see FIGS. 2 and 4 and FIG. 5 bottom). The tabs 18 may be arranged on all sides of an inner circumference of the lower rim 8. The liquid may accordingly flow from the interior 5 into the lower part of the hollow space 4 between the anti-piercing means 6 and the lower wall 2.

The lower wall 2 and the upper wall 1 may be elastically expandable. The hollow space 4 may then be elastically deformed or elastically expanded by injection of the liquid into the hollow space 4. The liquid in the hollow space 4 is then under an elastic pressure. As a result, the liquid can be expelled from the hollow space 4 through the feed-through 3. Before or also after, the implant may be implanted subcutaneously in the region of a joint or at another site to be treated. After exiting from the hollow space 4, the liquid can be spread and distributed through the feed-through 3 along the interspace between the lower side of the lower wall 2 and the substrate. Once liquid has ceased flowing out of the hollow space 4, either a pressure may be exerted on the implant in order to overcome back pressure and release further liquid from the implant or new liquid can be injected into the interior 5 with a syringe.

A method according to the invention is described in detail further below in relation to FIGS. 24 to 33 in connection with the ninth exemplary implant. The method can, however, also be straightforwardly transferred to the implant which has just been described.

The implant of the second exemplary embodiment according to FIGS. 6 to 8 differs from the first exemplary embodiment by two lugs 20 on an upper circumferential rim 27 of an upper wall 1 of the implant with which the implant can be sutured to soft tissue. Otherwise, the second implant is the same as the first implant according to FIGS. 1 to 5. The upper wall 1 is pierceable using manual force with a conventional medical injection cannula (as is shown for the ninth exemplary embodiment in FIGS. 27 to 33). The upper wall 1 may form an upper side of the implant. The material for the upper wall 1 may be such that, once an inserted injection cannula has been withdrawn, the upper wall 1 automatically closes back up. The upper wall 1 may to this end consist of a rubber-elastic plastics material or rubber, or at least in a central region include a rubber-elastic plastics material or rubber. Such self-sealing membranes may for example be used in vials for drawing up syringes.

A lower wall 2 with a feed-through 3 is arranged on the lower side of the implant which is opposite the upper side, wherein a plurality of feed-throughs (not shown) may also be provided. The feed-through 3 may be arranged centrally in the middle of the lower wall 2. The feed-through 3 connects the upper side of the lower wall 2 to the lower side of the upper wall 1 and thus to the lower side of the implant.

The upper wall 1 and the lower wall 2 delimit a hollow space 4 in the interior of the implant. The feed-through 3 liquid-permeably connects the hollow space 4 of the implant to the surroundings of the implant. An interior 5, which is a portion of the hollow space 4, may be arranged between an anti-piercing means 6 in the hollow space 4 and the upper wall 1. The anti-piercing means 6 is disk-shaped and is arranged in the hollow space 4 between the lower wall 2 and the upper wall 1. The anti-piercing means 6 may be disk-shaped. The anti-piercing means 6 may have a smaller diameter than the hollow space 4, such that it divides the hollow space 4 into two parts in non-liquid-tight manner, or into two regions liquid-permeably connected together. FIG. 20 shows the anti-piercing means 6 in detail. The anti-piercing means 6 is not pierceable using manual force with a conventional medical injection cannula (as is shown for the ninth exemplary embodiment in FIGS. 27 to 33).

The upper rim 27 of the upper wall 1 may form a circle which encloses the upper wall 1. The lower wall 2 may have a circumferential lower rim 8. The lower rim 8 of the lower wall 2 may form a circle which encloses the lower wall 2.

The lower wall 2 may have on a lower side bumps 10 which protrude from the lower side of the lower wall 2. In this manner it is possible to ensure that, when the implant is lying with the lower side of the lower wall 2 on a support, it maintains a space there. Thanks to the resultant interspace, the liquid which exits through the feed-through 3 from the hollow space 4 can then be distributed along the surface of the lower wall 2.

The anti-piercing means 6 may have an undulating shape which forms protruding patterning 12 on the upper side and the lower side of the anti-piercing means 6 (see FIG. 20). In this way, it is possible to ensure that a lower side of the upper wall 1 is spaced from an upper side of the anti-piercing means 6 in such a manner that the tip of an injection cannula can penetrate into the interior 5 in order to inject the liquid therein. In addition, an upper side of the lower wall 2 can accordingly be spaced from the lower side of the anti-piercing means 6, such that a liquid can be spread without any problem in the lower part of the interior 4 and be spread up to the feed-through 3.

The upper wall 1 and the lower wall 2 may be connected together in liquid-tight manner via the upper rim 27 and the lower rim 8, such that, apart from the feed-through 3, the hollow space 4 is closed in liquid-tight manner. To this end, a latching ring 24 may be formed on the upper rim 27 and a latching ring 16 on the lower rim 8. The latching ring 24 of the upper rim 27 is capable of engaging in the latching ring 16 of the lower rim 8 when the upper wall 1 is completely set in place on the lower wall 2.

The use of such an implant and thus a method according to the invention may proceed by an injection cannula of a syringe being inserted through the upper wall 1 in a central region. A liquid can then be injected from the syringe into the interior 5. The anti-piercing means 6 may be held centrally with the assistance of tabs (not visible, but similar to the tabs 18 according to the first exemplary embodiment) projecting into the hollow space 4, such that the anti-piercing means 6 is laterally spaced from the lower rim 8 (similar to FIGS. 2 and 4 and FIG. 5 bottom). The tabs may be arranged on all sides of an inner circumference of the lower rim 8. The liquid may accordingly flow from the interior 5 into the lower part of the hollow space 4 between the anti-piercing means 6 and the lower wall 2.

The lower wall 2 and the upper wall 1 may be elastically expandable. The hollow space 4 may then be elastically deformed or elastically expanded by injection of the liquid into the hollow space 4. The liquid in the hollow space 4 is then under an elastic pressure. As a result, the liquid can be expelled from the hollow space 4 through the feed-through 3. Before or also after, the implant may be implanted subcutaneously in the region of a joint or at another site to be treated and sutured to soft tissue and fixed in place with the assistance of the lugs 20. After exiting from the hollow space 4, the liquid can be spread and distributed through the feed-through 3 along the interspace between the lower side of the lower wall 2 and the substrate. Once liquid has ceased flowing out of the hollow space 4, either a pressure may be exerted on the implant in order to overcome back pressure and release further liquid from the implant or new liquid can be injected into the interior 5 with a syringe.

A method according to the invention is described in detail further below in relation to FIGS. 24 to 33 in connection with the ninth exemplary implant. The method can, however, also be straightforwardly transferred to the implant which has just been described.

The implant of the third exemplary embodiment according to FIGS. 9 to 11 differs from the first exemplary embodiment by a curved upper wall 31 and a differently shaped upper rim 37, in which are arranged a plurality of holes 39 or lugs 39 with which the implant can be sutured to soft tissue. Otherwise, the third implant is the same as the first implant according to FIGS. 1 to 5. The upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

A lower wall 2 with a feed-through 3 is arranged on the lower side of the implant which is opposite the upper side, wherein a plurality of feed-throughs (not shown) may also be provided. The feed-through 3 may be arranged centrally in the middle of the lower wall 2. The feed-through 3 connects the upper side of the lower wall 2 to the lower side of the upper wall 1 and thus to the lower side of the implant.

The upper wall 31 and the lower wall 2 delimit a hollow space 34 in the interior of the implant. The feed-through 3 liquid-permeably connects the hollow space 34 of the implant to the surroundings of the implant. An interior 35, which is a portion of the hollow space 34, may be arranged between an anti-piercing means 6 in the hollow space 34 and the upper wall 31. The anti-piercing means 6 is disk-shaped and is arranged in the hollow space 34 between the lower wall 2 and the upper wall 31. The anti-piercing means 6 may be disk-shaped. The anti-piercing means 6 may have a smaller diameter than the hollow space 34, such that it divides the hollow space 34 into two parts in non-liquid-tight manner, or into two regions liquid-permeably connected together. FIG. 20 shows the anti-piercing means 6 in detail. The anti-piercing means 6 is not pierceable using manual force with a medical injection cannula (as is shown for the ninth exemplary embodiment in FIGS. 27 to 33).

The upper rim 37 of the upper wall 31 may form a circle which encloses the upper wall 31. The lower wall 2 may have a circumferential lower rim 8. The lower rim 8 of the lower wall 2 may form a circle which encloses the lower wall 2.

The lower wall 2 may have on a lower side bumps 10 which protrude from the lower side of the lower wall 2. In this manner it is possible to ensure that, when the implant is lying with the lower side of the lower wall 2 on a support, it maintains a space there. Thanks to the resultant interspace, the liquid which exits through the feed-through 3 from the hollow space 34 can then be distributed along the surface of the lower wall 2.

The anti-piercing means 6 may have an undulating shape which forms protruding patterning 12 on the upper side and the lower side of the anti-piercing means 6 (see FIG. 20). In this way, it is possible to ensure that a lower side of the upper wall 31 is spaced from an upper side of the anti-piercing means 6 in such a manner that the tip of an injection cannula can penetrate into the interior 35 in order to inject the liquid therein. In addition, an upper side of the lower wall 2 can accordingly be spaced from the lower side of the anti-piercing means 6, such that a liquid can be spread without any problem in the lower part of the interior 34 and spread up to the feed-through 3.

The upper wall 31 and the lower wall 2 may be connected together in liquid-tight manner via the upper rim 37 and the lower rim 8, such that, apart from the feed-through 3, the hollow space 34 is closed in liquid-tight manner. To this end, a latching ring 34 may be formed on the upper rim 37 and a latching ring 16 on the lower rim 8. The latching ring 34 of the upper rim 37 is capable of engaging in the latching ring 16 of the lower rim 8 when the upper wall 31 is completely set in place on the lower wall 2.

The use of such an implant and thus a method according to the invention may proceed by an injection cannula of a syringe being inserted through the upper wall 31 in a central region. A liquid can then be injected from the syringe into the interior 35. The anti-piercing means 6 may be held centrally with the assistance of tabs (not visible, but similar to the tabs 18 according to the first exemplary embodiment) projecting into the hollow space 34, such that the anti-piercing means 6 is laterally spaced from the lower rim 8 (similar to FIGS. 2 and 4 and FIG. 5 bottom). The tabs may be arranged on all sides of an inner circumference of the lower rim 8. The liquid may accordingly flow from the interior 35 into the lower part of the hollow space 34 between the anti-piercing means 6 and the lower wall 2.

The lower wall 2 and the upper wall 31 may be elastically expandable. The hollow space 34 may then be elastically deformed or elastically expanded by injection of the liquid into the hollow space 34. The liquid in the hollow space 34 is then under an elastic pressure. As a result, the liquid can be expelled from the hollow space 34 through the feed-through 3. Before or also after, the implant may be implanted subcutaneously in the region of a joint or at another site to be treated and sutured to soft tissue and fixed in place with the assistance of the lugs 39. After exiting from the hollow space 34, the liquid can be spread and distributed through the feed-through 3 along the interspace between the lower side of the lower wall 2 and the substrate. Once liquid has ceased flowing out of the hollow space 34, either a pressure may be exerted on the implant in order to overcome back pressure and release further liquid from the implant or new liquid can be injected into the interior 35 with a syringe.

A method according to the invention is described in detail further below in relation to FIGS. 24 to 33 in connection with the ninth exemplary implant. The method can, however, also be straightforwardly transferred to the implant which has just been described.

Figure 12:
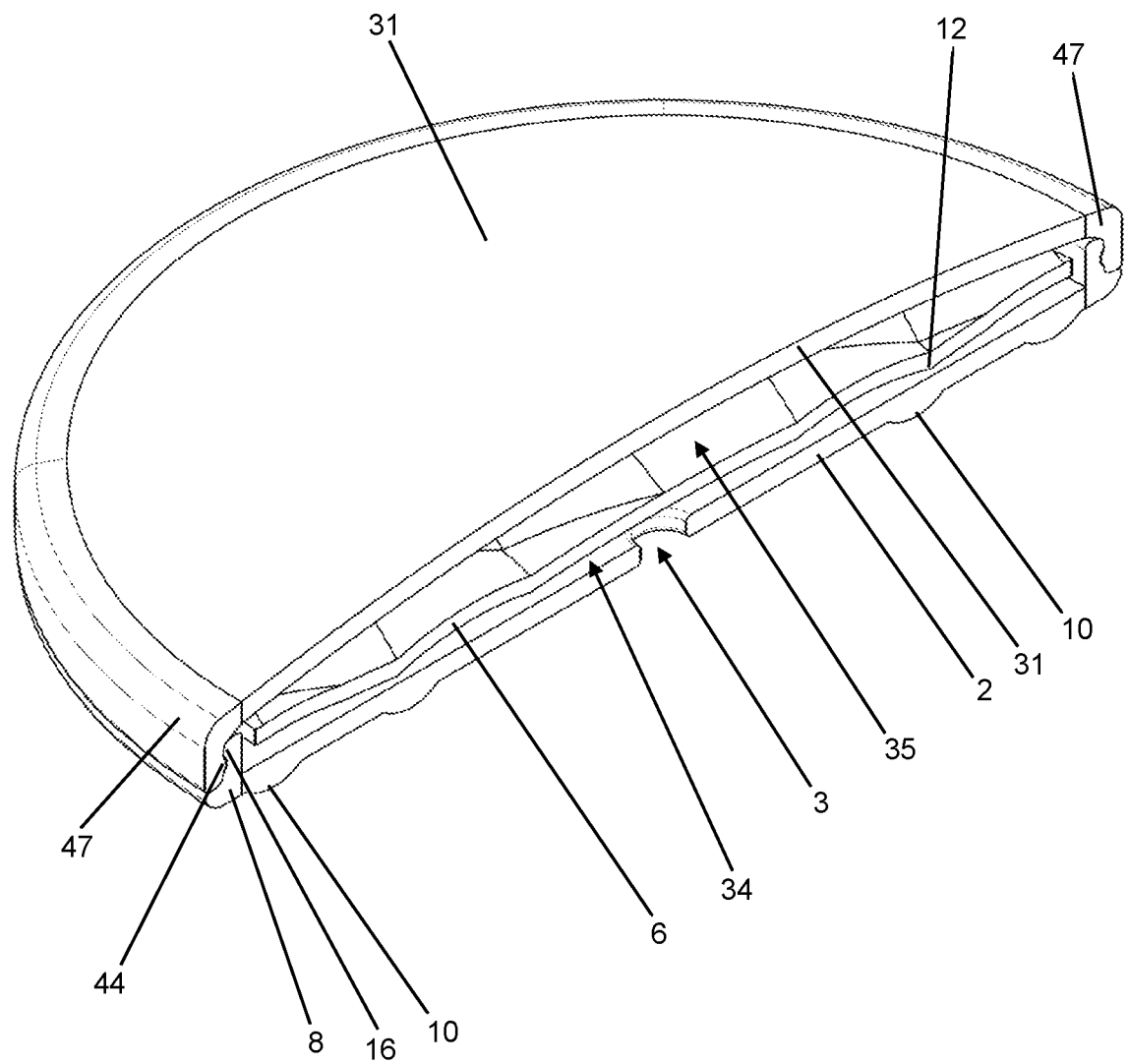
FIG. 12 is a schematic perspective cross-sectional view through a fourth exemplary implant for the local administration of liquids.
Figure 13:
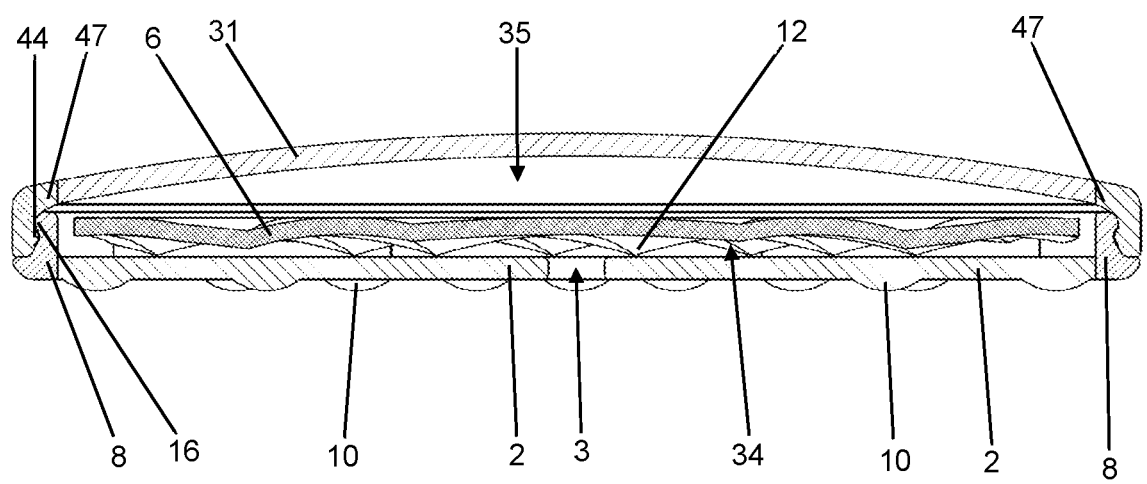
FIG. 13 is a schematic cross-sectional view of the fourth implant according to FIG. 12.

The implant of the fourth exemplary embodiment according to FIGS. 12 and 13 differs from the first exemplary embodiment by a curved upper wall 31. Otherwise, the fourth implant is the same as the first implant according to FIGS. 1 to 5. The upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

A lower wall 2 with a feed-through 3, with bumps 10 and a lower rim 8, is arranged on the lower side of the implant which is opposite the upper side, wherein the lower wall 2 is of similar structure to the first exemplary embodiment.

The upper wall 31 and the lower wall 2 delimit a hollow space 34 in the interior of the implant. Similarly to the first exemplary embodiment, an anti-piercing means 6 is arranged in the hollow space 34 as shown in FIG. 20.

An upper rim 47 of the upper wall 31 may form a circle which encloses the upper wall 31.

The upper wall 31 and the lower wall 2 may be connected together in liquid-tight manner via the upper rim 47 and the lower rim 8, such that, apart from the feed-through 3, the hollow space 34 is closed in liquid-tight manner. To this end, a latching ring 44 may be formed on the upper rim 47 and a latching ring 16 on the lower rim 8. The latching ring 44 of the upper rim 47 is capable of engaging in the latching ring 16 of the lower rim 8 when the upper wall 31 is completely set in place on the lower wall 2.

The use of such an implant and thus a method according to the invention proceeds similarly to the first exemplary embodiment.

A method according to the invention is described in detail further below in relation to FIGS. 24 to 33 in connection with the ninth exemplary implant. The method can, however, also be straightforwardly transferred to the implant which has just been described.

Figure 14:
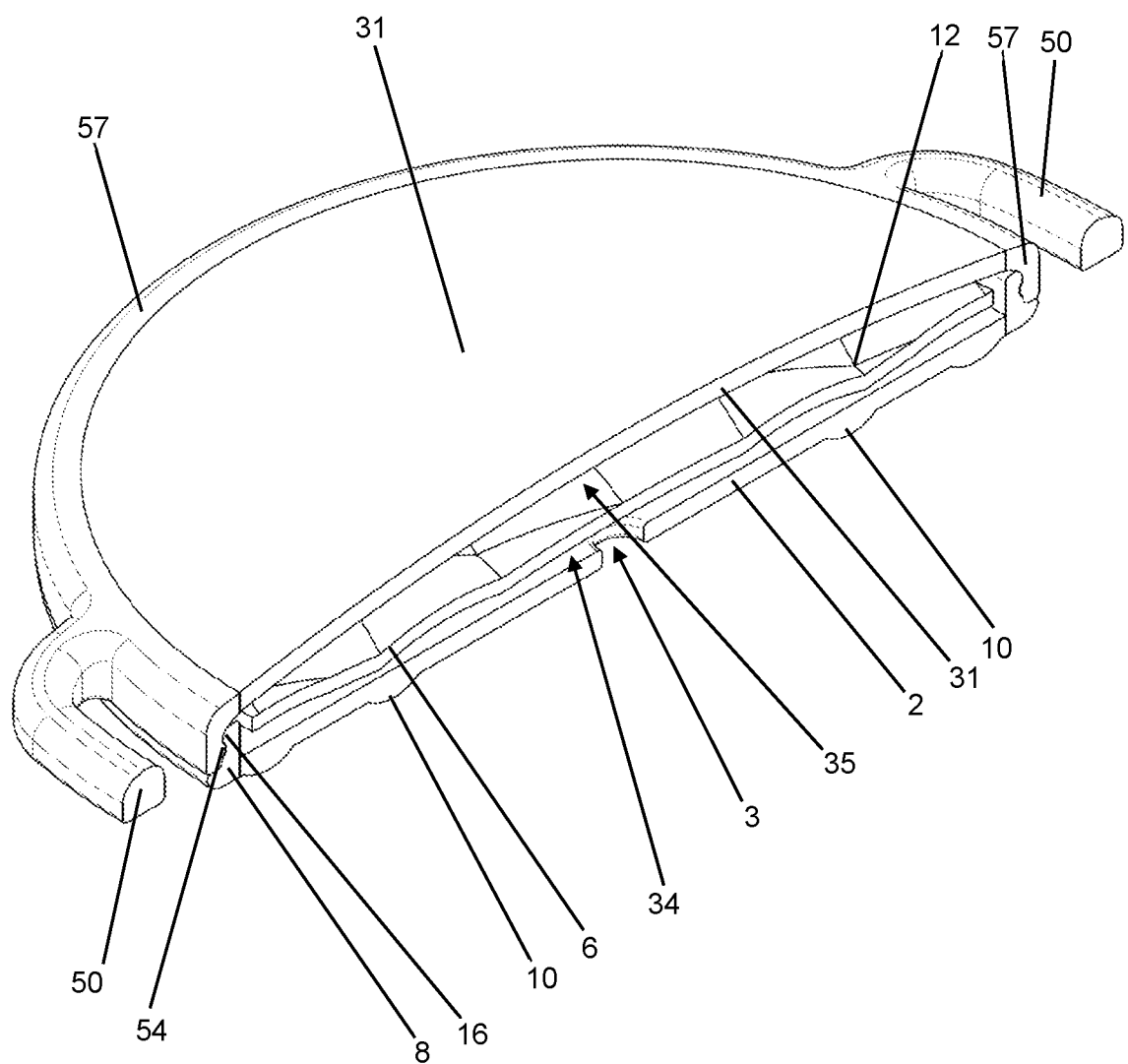
FIG. 14 is a schematic perspective cross-sectional view through a fifth exemplary implant for the local administration of liquids.
Figure 15:
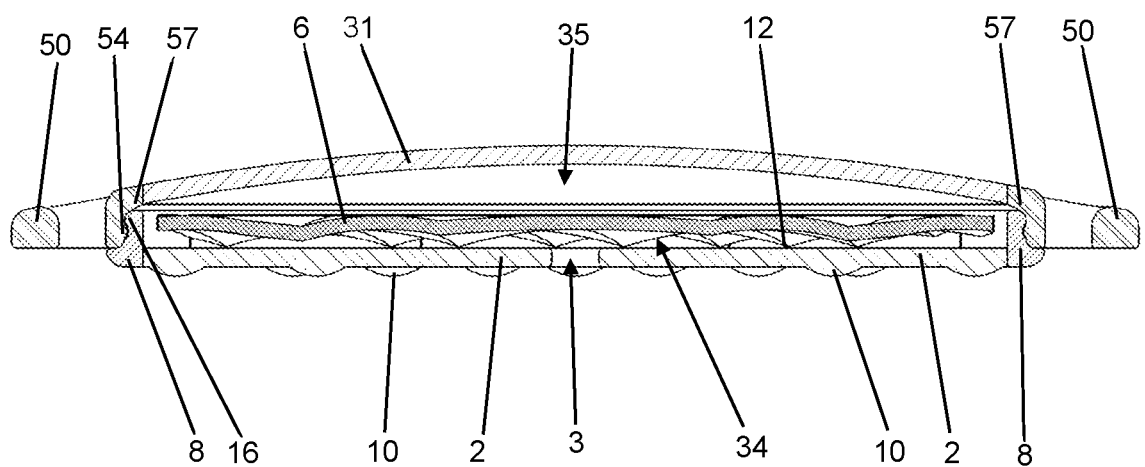
FIG. 15 is a schematic cross-sectional view of the fifth implant according to FIG. 14.

The implant of the fifth exemplary embodiment according to FIGS. 14 and 15 differs from the second exemplary embodiment by a curved upper wall 31. Otherwise, the fifth implant is the same as the second implant according to FIGS. 6 to 8 and thus, similarly to the second implant, has two lateral lugs 50 on an upper rim 57 of the upper wall 31, with which the fifth implant can be sutured to soft tissue and fixed in place there. The upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

A lower wall 2 with a feed-through 3, with bumps 10 and a lower rim 8, is arranged on the lower side of the implant which is opposite the upper side, wherein the lower wall 2 is of similar structure to the first and second exemplary embodiments.

The upper wall 31 and the lower wall 2 delimit a hollow space 34 in the interior of the implant. Similarly to the first exemplary embodiment, an anti-piercing means 6 is arranged in the hollow space 34 as shown in FIG. 20.

The upper rim 57 of the upper wall 31 may form a circle which encloses the upper wall 31. The upper wall 31 and the lower wall 2 may be connected together in liquid-tight manner via the upper rim 57 and the lower rim 8, such that, apart from the feed-through 3, the hollow space 34 is closed in liquid-tight manner. To this end, a latching ring 54 may be formed on the upper rim 57 and a latching ring 16 on the lower rim 8. The latching ring 54 of the upper rim 57 is capable of engaging in the latching ring 16 of the lower rim 8 when the upper wall 31 is completely set in place on the lower wall 2.

The use of such an implant and thus a method according to the invention proceeds similarly to the second exemplary embodiment.

A method according to the invention is described in detail further below in relation to FIGS. 24 to 33 in connection with the ninth exemplary implant. The method can, however, also be straightforwardly transferred to the implant which has just been described.

Figure 16:
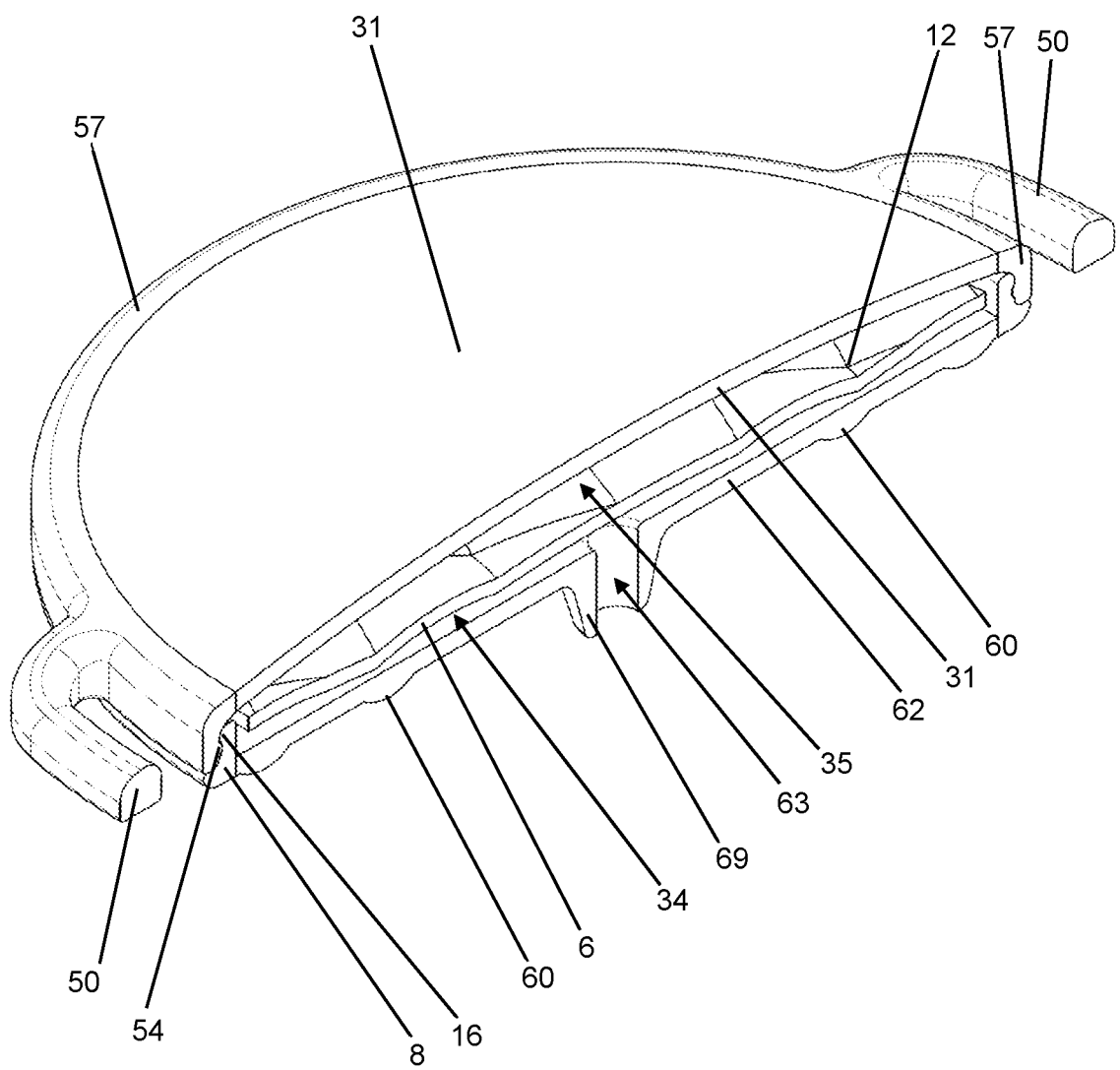
FIG. 16 is a schematic perspective cross-sectional view through a sixth exemplary implant for the local administration of liquids.
Figure 17:
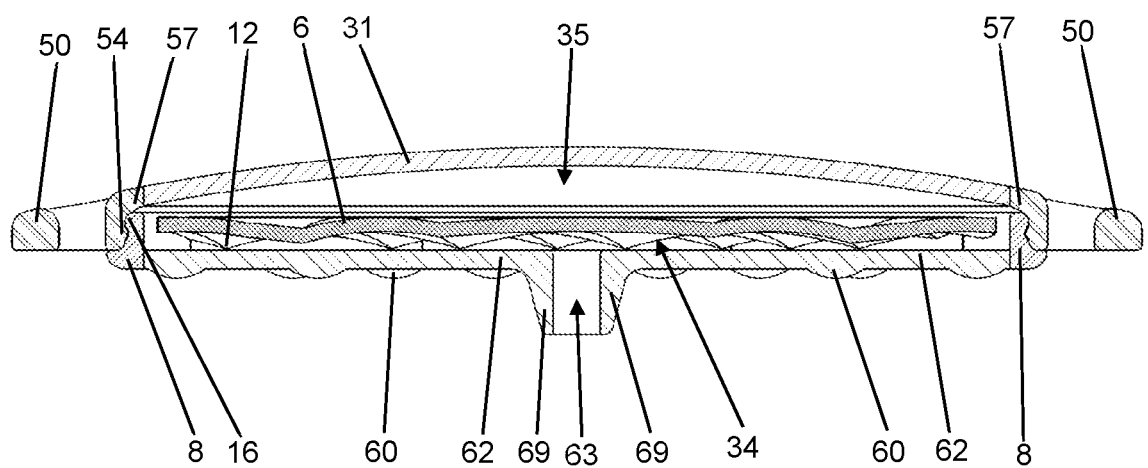
FIG. 17 is a schematic cross-sectional view of the sixth implant according to FIG. 16.

The implant of the sixth exemplary embodiment according to FIGS. 16 and 17 differs from the fifth exemplary embodiment by a lower wall 62 with a tube 69 on the lower side of the lower wall 62. Otherwise, the sixth implant is the same as the fifth implant according to FIGS. 14 to 15 and thus, similarly to the fifth implant, has two lateral lugs 50 on an upper rim 57 of the upper wall 31, with which the sixth implant can be sutured to soft tissue and fixed in place there. The upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

The lower wall 62 with a feed-through 63 is arranged on the lower side of the implant which is opposite the upper side, wherein a plurality of feed-throughs (not shown) may also be provided. The feed-through 63 is cylindrical and extends through the tube 69. The feed-through 63 and tube 69 may be arranged centrally in the middle of the lower wall 62. The feed-through 63 connects the upper side of the lower wall 62 to the lower side of the upper wall 31 and thus to the lower side of the implant.

The upper wall 31 and the lower wall 62 delimit a hollow space 34 in the interior of the implant. The feed-through 63 liquid-permeably connects the hollow space 34 of the implant to the surroundings of the implant. An interior 35, which is a portion of the hollow space 34, may be arranged between an anti-piercing means 6 in the hollow space 34 and the upper wall 31. The anti-piercing means 6 is disk-shaped and is arranged in the hollow space 34 between the lower wall 62 and the upper wall 31. The anti-piercing means 6 may be disk-shaped. The anti-piercing means 6 may have a smaller diameter than the hollow space 34, such that it divides the hollow space 34 into two parts in non-liquid-tight manner, or into two regions liquid-permeably connected together. FIG. 20 shows the anti-piercing means 6 in detail. The anti-piercing means 6 is not pierceable using manual force with a conventional medical injection cannula (as is shown for the ninth exemplary embodiment in FIGS. 27 to 33).

The upper rim 57 of the upper wall 31 may form a circle which encloses the upper wall 31. The lower wall 62 may have a circumferential lower rim 8. The lower rim 8 of the lower wall 62 may form a circle which encloses the lower wall 62.

The lower wall 62 may have on a lower side bumps 60 which protrude from the lower side of the lower wall 62. In this manner it is possible to ensure that, when the implant is lying with the lower side of the lower wall 62 around the tube 69 on a support, it maintains a space there. Thanks to the resultant interspace, the liquid which exits through the feed-through 63 and through the tube 69 from the hollow space 34 can then be distributed along the surface of the lower wall 62. Using the tube 69, the liquid can be administered in an indentation in the substrate, such as for example in a cavity on a joint.

The anti-piercing means 6 may have an undulating shape which forms protruding patterning 12 on the upper side and the lower side of the anti-piercing means 6 (see FIG. 20). In this way, it is possible to ensure that a lower side of the upper wall 31 is spaced from an upper side of the anti-piercing means 6 in such a manner that the tip of an injection cannula can penetrate into the interior 35 in order to inject the liquid therein. In addition, an upper side of the lower wall 62 can accordingly be spaced from the lower side of the anti-piercing means 6, such that a liquid can be spread without any problem in the lower part of the interior 34 and spread up to the feed-through 63.

The upper wall 31 and the lower wall 62 may be connected together in liquid-tight manner via the upper rim 57 and the lower rim 8, such that, apart from the feed-through 63, the hollow space 34 is closed in liquid-tight manner. To this end, a latching ring 54 may be formed on the upper rim 57 and a latching ring 16 on the lower rim 8. The latching ring 54 of the upper rim 57 is capable of engaging in the latching ring 16 of the lower rim 8 when the upper wall 31 is completely set in place on the lower wall 62.

The use of such an implant and thus a method according to the invention may proceed by an injection cannula of a syringe being inserted through the upper wall 31 in a central region. A liquid can then be injected from the syringe into the interior 35. The anti-piercing means 6 may be held centrally with the assistance of tabs (not visible, but similar to the tabs 18 according to the first exemplary embodiment) projecting into the hollow space 34, such that the anti-piercing means 6 is laterally spaced from the lower rim 8 (similar to FIGS. 2 and 4 and FIG. 5 bottom). The tabs may be arranged on all sides of an inner circumference of the lower rim 8. The liquid may accordingly flow from the interior 35 into the lower part of the hollow space 34 between the anti-piercing means 6 and the lower wall 62.

The lower wall 62 and the upper wall 31 may be elastically expandable. The hollow space 34 may then be elastically deformed or elastically expanded by injection of the liquid into the hollow space 34. The liquid in the hollow space 34 is then under an elastic pressure. As a result, the liquid can be expelled from the hollow space 34 through the feed-through 63. Before or also after, the implant may be implanted subcutaneously in the region of a joint or at another site to be treated and sutured to soft tissue and fixed in place with the assistance of the lugs 50. After exiting from the hollow space 34, the liquid can be spread and distributed through the feed-through 63 along the tube 69 and along the interspace between the lower side of the lower wall 62 around the tube 69 and the substrate. Once liquid has ceased flowing out of the hollow space 34, either a pressure may be exerted on the implant in order to overcome back pressure and release further liquid from the implant or new liquid can be injected into the interior 35 with a syringe.

A method according to the invention is described in detail further below in relation to FIGS. 24 to 33 in connection with the ninth exemplary implant. The method can, however, also be straightforwardly transferred to the implant which has just been described.

Figure 18:
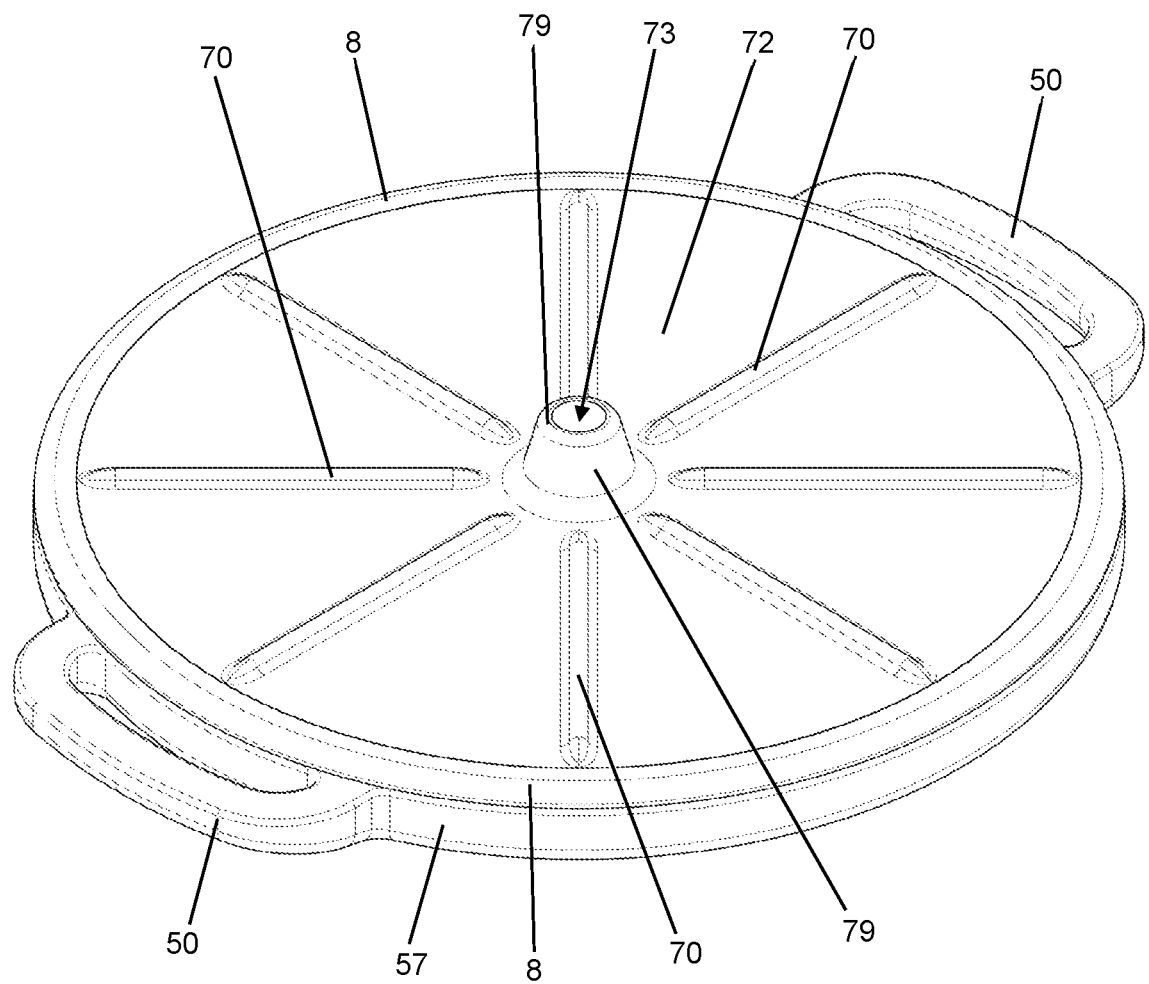
FIG. 18 is a schematic perspective plan view onto the lower side of a seventh exemplary implant for the local administration of liquids.
Figure 19:
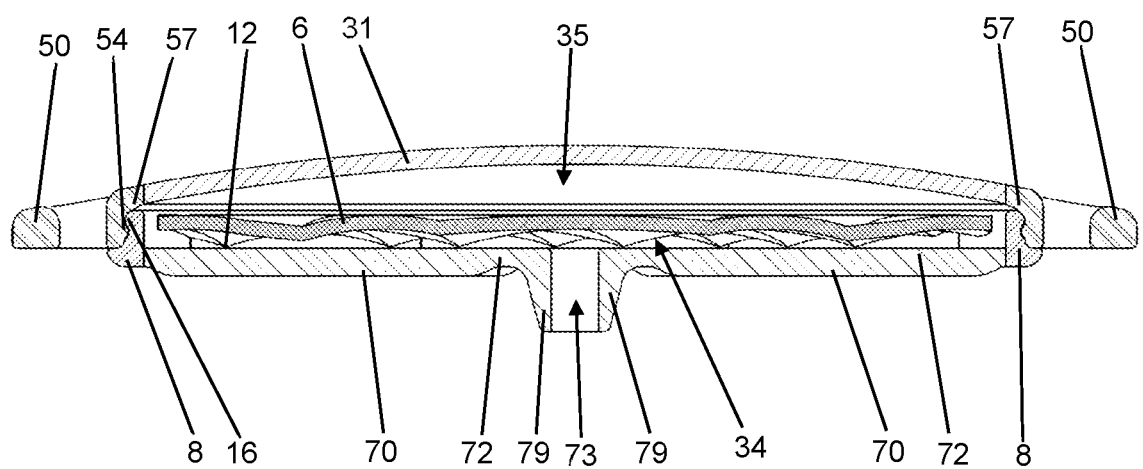
FIG. 19 is a schematic cross-sectional view of the seventh implant according to FIG. 18.

The implant of the seventh exemplary embodiment according to FIGS. 18 and 19 differs from the sixth exemplary embodiment according to FIGS. 16 and 17 by radial ribs 70 instead of bumps 60. Otherwise, the seventh implant is the same as the sixth implant according to FIGS. 16 to 17 and thus, similarly to the sixth implant, has a tube 79 for forming a feed-through 73 through a lower wall 72 and has two lateral lugs 50 on an upper rim 57 of the upper wall 31, with which the fifth implant can be sutured to soft tissue and fixed in place there. The upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

The lower wall 72 with the tube 79 and the feed-through 73, with ribs 70 and a lower rim 8, is arranged on the lower side of the implant which is opposite the upper side. The liquid from the implant can be guided radially outward along the ribs 70. The ribs 70 here ensure a free interspace between a substrate of the implant and the lower side of the implant.

The upper wall 31 and the lower wall 72 delimit a hollow space 34 in the interior of the implant. Similarly to the first exemplary embodiment, an anti-piercing means 6 which is shown in FIG. 20 is arranged in the hollow space 34.

The use of such an implant and thus a method according to the invention proceeds similarly to the sixth exemplary embodiment.

A method according to the invention is described in detail further below in relation to FIGS. 24 to 33 in connection with the ninth exemplary implant. The method can, however, also be straightforwardly transferred to the implant which has just been described.

The implant of the eighth exemplary embodiment according to FIGS. 21 to 23 differs from the fifth exemplary embodiment by a modified anti-piercing means 86 which is shown in FIG. 23. Otherwise, the eighth implant is the same as the fifth implant according to FIGS. 14 to 15 and thus, similarly to the fifth implant, has two lateral lugs 50 on an upper rim 57 of the upper wall 31, with which the eighth implant can be sutured to soft tissue and fixed in place there. The curved upper wall 31 is pierceable using manual force with a conventional medical injection cannula (as is shown for the ninth exemplary embodiment in FIGS. 27 to 33). The upper wall 31 may form an upper side of the implant. The material for the upper wall 31 may be such that, once an inserted injection cannula has been withdrawn, the upper wall 31 automatically closes back up. The upper wall 31 may to this end consist of a rubber-elastic plastics material or rubber, or at least in a central region include a rubber-elastic plastics material or rubber. Such self-sealing membranes may for example be used in vials for drawing up syringes.

The lower wall 2 with a feed-through 3 is arranged on the lower side of the implant which is opposite the upper side, wherein a plurality of feed-throughs (not shown) may also be provided. The feed-through 3 may be arranged centrally in the middle of the lower wall 2. The feed-through 3 connects the upper side of the lower wall 2 to the lower side of the upper wall 1 and thus to the lower side of the implant.

The upper wall 31 and the lower wall 2 delimit a hollow space 84 in the interior of the implant. The feed-through 3 liquid-permeably connects the hollow space 84 of the implant to the surroundings of the implant. An interior 85, which is a portion of the hollow space 84, may be arranged between the anti-piercing means 86 in the hollow space 84 and the upper wall 31. The anti-piercing means 86 is disk-shaped and is arranged in the hollow space 84 between the lower wall 2 and the upper wall 31. The anti-piercing means 86 may be disk-shaped and have protruding surface patterning 82 on the lower side thereof. The anti-piercing means 86 may have a smaller diameter than the hollow space 84, such that it divides the hollow space 84 into two parts in non-liquid-tight manner, or into two regions liquid-permeably connected together. FIG. 23 shows the anti-piercing means 86 in detail. The anti-piercing means 86 is not pierceable using manual force with a conventional medical injection cannula (as is shown for the ninth exemplary embodiment in FIGS. 27 to 33).

The upper rim 57 of the upper wall 31 may form a circle which encloses the upper wall 31. The lower wall 2 may have a circumferential lower rim 8. The lower rim 8 of the lower wall 2 may form a circle which encloses the lower wall 2.

The lower wall 2 may have on a lower side bumps 10 which protrude from the lower side of the lower wall 2. In this manner it is possible to ensure that, when the implant is lying with the lower side of the lower wall 2 on a support, it maintains a space there. Thanks to the resultant interspace, the liquid which exits through the feed-through 3 from the hollow space 84 can then be distributed along the surface of the lower wall 2.

The anti-piercing means 86 may have a planar shape with surface patterning 82 protruding from the lower side of the anti-piercing means 86 (see FIG. 23). It may thus be ensured that an upper side of the lower wall 2 is spaced from the lower side of the anti-piercing means 86, such that a liquid can be spread without any problem in the lower part of the interior 84 and be spread up to the feed-through 3.

The upper wall 31 and the lower wall 2 may be connected together in liquid-tight manner via the upper rim 57 and the lower rim 8, such that, apart from the feed-through 3, the hollow space 84 is closed in liquid-tight manner. To this end, a latching ring 54 may be formed on the upper rim 57 and a latching ring 16 on the lower rim 8. The latching ring 54 of the upper rim 57 is capable of engaging in the latching ring 16 of the lower rim 8 when the upper wall 31 is completely set in place on the lower wall 2.

The use of such an implant and thus a method according to the invention may proceed by an injection cannula of a syringe being inserted through the upper wall 31 in a central region. A liquid can then be injected from the syringe into the interior 85. The anti-piercing means 86 may be held centrally with the assistance of tabs (not visible, but similar to the tabs 18 according to the first exemplary embodiment) projecting into the hollow space 84, such that the anti-piercing means 86 is laterally spaced from the lower rim 8 (similar to FIGS. 2 and 4 and FIG. 5 bottom). The tabs may be arranged on all sides of an inner circumference of the lower rim 8. The liquid may accordingly flow from the interior 85 into the lower part of the hollow space 84 between the anti-piercing means 86 and the lower wall 2.

The lower wall 2 and the upper wall 31 may be elastically expandable. The hollow space 84 may then be elastically deformed or elastically expanded by injection of the liquid into the hollow space 84. The liquid in the hollow space 84 is then under an elastic pressure. As a result, the liquid can be expelled from the hollow space 84 through the feed-through 3. Before or also after, the implant may be implanted subcutaneously in the region of a joint or at another site to be treated and sutured to soft tissue and fixed in place with the assistance of the lugs 50. After exiting from the hollow space 84, the liquid can be spread and distributed through the feed-through 3 and along the interspace between the lower side of the lower wall 2 and the substrate. Once liquid has ceased flowing out of the hollow space 84, either a pressure may be exerted on the implant in order to overcome back pressure and release further liquid from the implant or new liquid can be injected into the interior 85 with a syringe.

A method according to the invention is described in detail further below in relation to FIGS. 24 to 33 in connection with the ninth exemplary implant. The method can, however, also be straightforwardly transferred to the implant which has just been described.

The implant of the ninth exemplary embodiment according to FIGS. 24 to 26 differs from the eighth exemplary embodiment by a modified anti-piercing means 96 which is shown in FIG. 26. Otherwise, the ninth implant is the same as the eighth implant according to FIGS. 21 to 23 and thus, similarly to the eighth implant, has two lateral lugs 50 on an upper rim 57 of the upper wall 31, with which the ninth implant can be sutured to soft tissue and fixed in place there. The course of a method according to the invention is shown in FIGS. 27 to 33 with reference to the ninth exemplary embodiment.

The curved upper wall 31 is pierceable using manual force with a conventional medical injection cannula 100, as is shown in FIGS. 27 to 33. The upper wall 31 may form an upper side of the implant. The material for the upper wall 31 may be such that, once the inserted medical injection cannula 100 has been withdrawn, the upper wall 31 automatically closes back up (see FIG. 30). The upper wall 31 may to this end consist of a rubber-elastic plastics material or rubber, or at least in a central region include a rubber-elastic plastics material or rubber. Such self-sealing membranes may for example be used in vials for drawing up syringes.

The lower wall 2 with a feed-through 3 is arranged on the lower side of the implant which is opposite the upper side, wherein a plurality of feed-throughs (not shown) may also be provided. The feed-through 3 may be arranged centrally in the middle of the lower wall 2. The feed-through 3 connects the upper side of the lower wall 2 to the lower side of the upper wall 1 and thus to the lower side of the implant.

The upper wall 31 and the lower wall 2 delimit a hollow space 94 in the interior of the implant. The feed-through 3 liquid-permeably connects the hollow space 94 of the implant to the surroundings of the implant. An interior 95, which is a portion of the hollow space 94, may be arranged between the anti-piercing means 96 in the hollow space 94 and the upper wall 31. The anti-piercing means 96 is disk-shaped and is arranged in the hollow space 94 between the lower wall 2 and the upper wall 31. The anti-piercing means 96 may be disk-shaped and have protruding surface patterning 92 on the lower side thereof as well as protruding surface patterning 99 on the upper side thereof. The anti-piercing means 96 may have a smaller diameter than the hollow space 94, such that it divides the hollow space 94 into two parts in non-liquid-tight manner, or into two regions liquid-permeably connected together. FIG. 26 shows the anti-piercing means 96 in detail. The anti-piercing means 96 is not pierceable using manual force with the medical injection cannula 100 of a syringe 102, as is shown in FIGS. 27 to 33.

The upper rim 57 of the upper wall 31 may form a circle which encloses the upper wall 31. The lower wall 2 may have a circumferential lower rim 8. The lower rim 8 of the lower wall 2 may form a circle which encloses the lower wall 2.

The lower wall 2 may have on a lower side bumps 10 which protrude from the lower side of the lower wall 2. In this manner it is possible to ensure that, when the implant is lying with the lower side of the lower wall 2 on a support, it maintains a space there. Thanks to the resultant interspace, the liquid which exits through the feed-through 3 from the hollow space 94 can then be distributed along the surface of the lower wall 2.

The anti-piercing means 96 may have a planar shape with surface patterning 92 protruding from the lower side of the anti-piercing means 96 and with surface patterning 99 protruding from the upper side of the anti-piercing means 96 (see FIG. 26). With the surface patterning 99 on the upper side of the anti-piercing means 96, it is possible to ensure that a lower side of the upper wall 31 is spaced from an upper side of the anti-piercing means 96 in such a manner that the tip of the injection cannula 100 can penetrate into the interior 95 in order to inject the liquid therein. In addition, an upper side of the lower wall 2 can be spaced from the lower side of the anti-piercing means 96 with the surface patterning 92 of the lower side of the anti-piercing means 96, such that a liquid can be spread without any problem in the lower part of the interior 94 and be spread up to the feed-through 3.

The upper wall 31 and the lower wall 2 may be connected together in liquid-tight manner via the upper rim 57 and the lower rim 8, such that, apart from the feed-through 3, the hollow space 94 is closed in liquid-tight manner. To this end, a latching ring 54 may be formed on the upper rim 57 and a latching ring 16 on the lower rim 8. The latching ring 54 of the upper rim 57 is capable of engaging in the latching ring 16 of the lower rim 8 when the upper wall 31 is completely set in place on the lower wall 2.

The course of a method according to the invention is explained below on the basis of the ninth implant and with reference to FIGS. 24 to 33. The syringe 102 and the implant which is not filled with liquid are provided (see FIG. 27). The syringe 102 has on the front side thereof the medical injection cannula 100. An interior of the syringe 102 delimited by a cartridge 104 can be filled with a liquid 114 by the injection cannula 100. The injection cannula 100 is connected to the cartridge 104 via a cartridge head 106. With the assistance of a piston 112, which can be advanced in the cartridge 104 in the direction of the injection cannula 100 via a plunger 108 with a grip 110, the contents of the syringe 102 can be administered from the cartridge 104 through the injection cannula 100.

Figure 28:
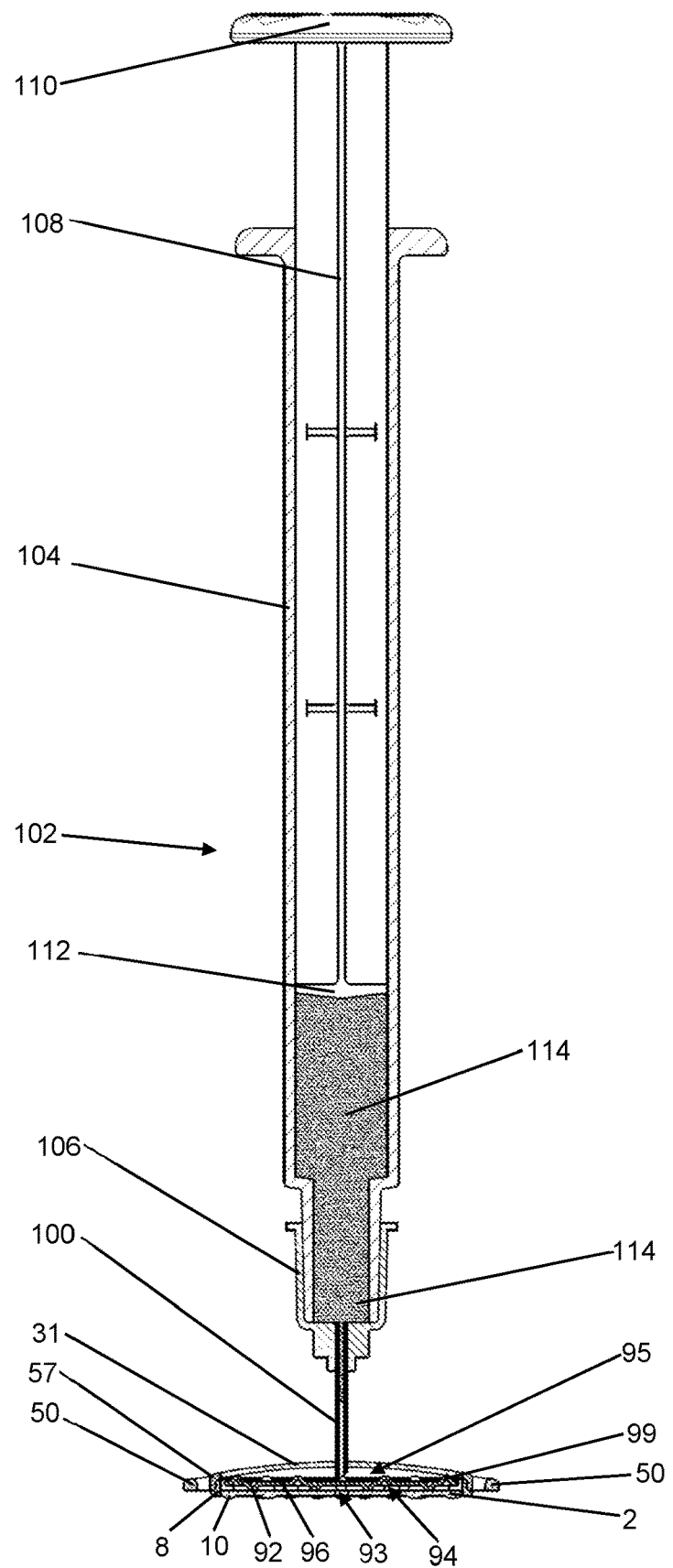
FIG. 28 is a schematic cross-sectional view through the ninth implant and the syringe inserted into the ninth implant shortly before filling of the ninth implant with a liquid from the syringe.
Figure 29:
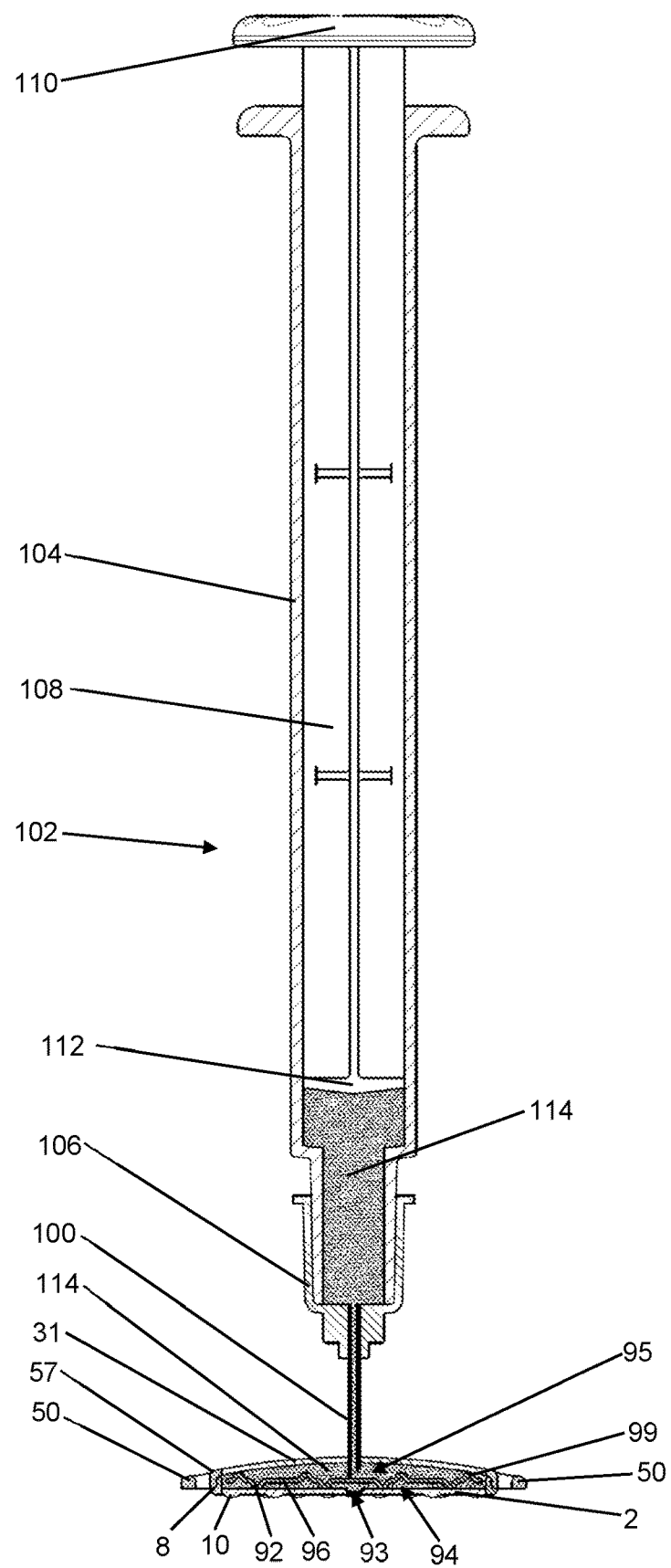
FIG. 29 is a schematic cross-sectional view through the ninth implant and the syringe inserted into the ninth implant during filling of the ninth implant with a liquid from the syringe.
Figure 32:
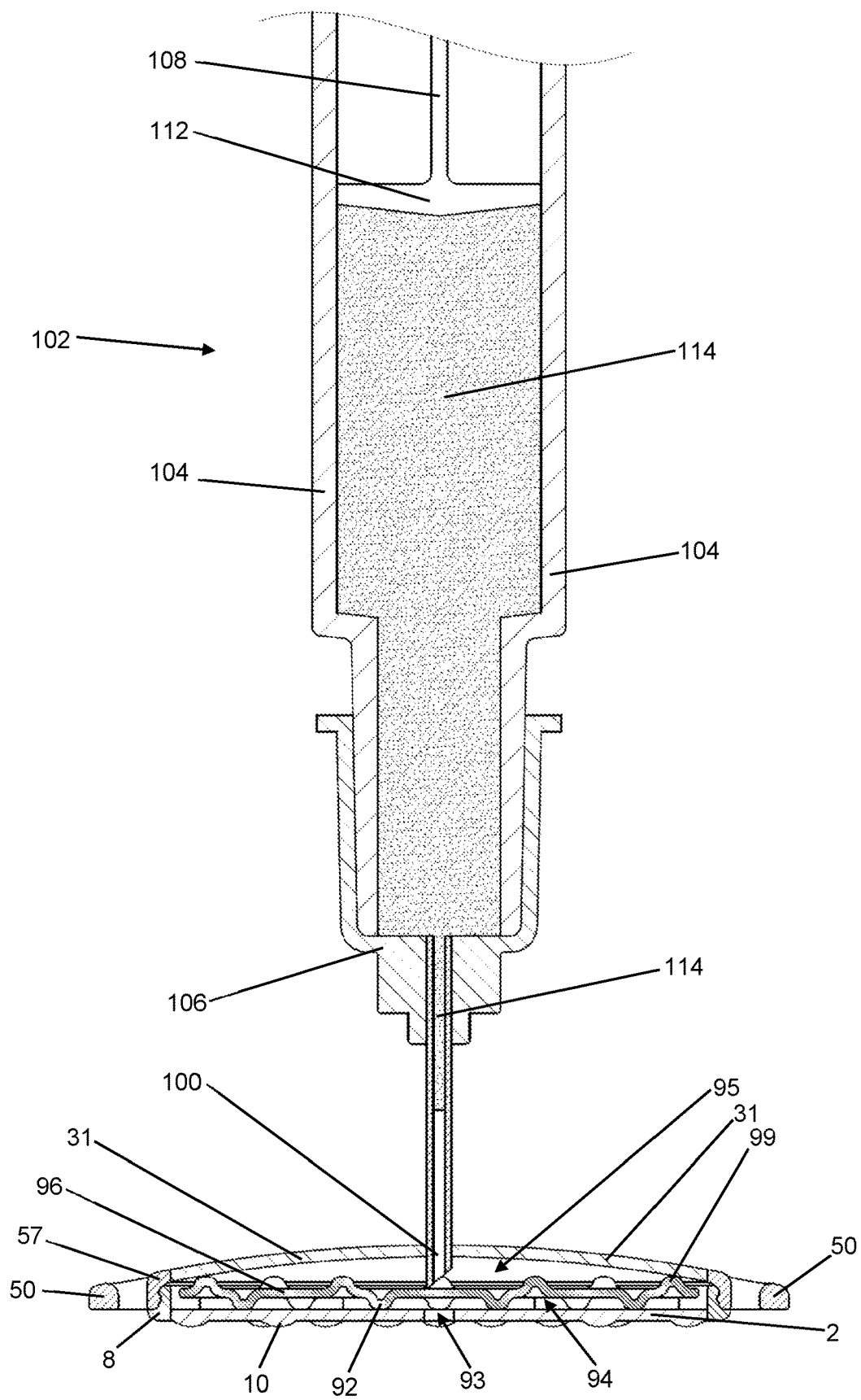
FIG. 32 is a detail view of the ninth implant with inserted injection cannula as an enlarged detail of FIG. 28.

The injection cannula 100 of the syringe 102 filled with liquid 114 is inserted through the upper wall 31 in a central region (FIGS. 28 and 32). The liquid 114 contains at least one active pharmaceutical ingredient, in particular cyclosporin A.

The liquid 114 is then injected from the syringe 102 into the interior 95 (see FIG. 29) by pressing the piston 112 with the assistance of the grip 110 and the plunger 108 in the direction of the injection cannula 100. The anti-piercing means 96 may be held centrally with the assistance of tabs (not visible, but similar to the tabs 18 according to the first exemplary embodiment) projecting into the hollow space 94, such that the anti-piercing means 96 is laterally spaced from the lower rim 8 (similar to FIGS. 2 and 4 and FIG. 5 bottom). The tabs may be arranged on all sides of an inner circumference of the lower rim 8. The liquid may accordingly flow from the interior 95 into the lower part of the hollow space 94 between the anti-piercing means 96 and the lower wall 2. Alternatively or additionally, openings (not shown) in the anti-piercing means 96 may also be provided, through which the liquid can flow from the interior 95 into the lower part of the hollow space 94. This modification may also be applied to all the other exemplary embodiments.

Figure 30:
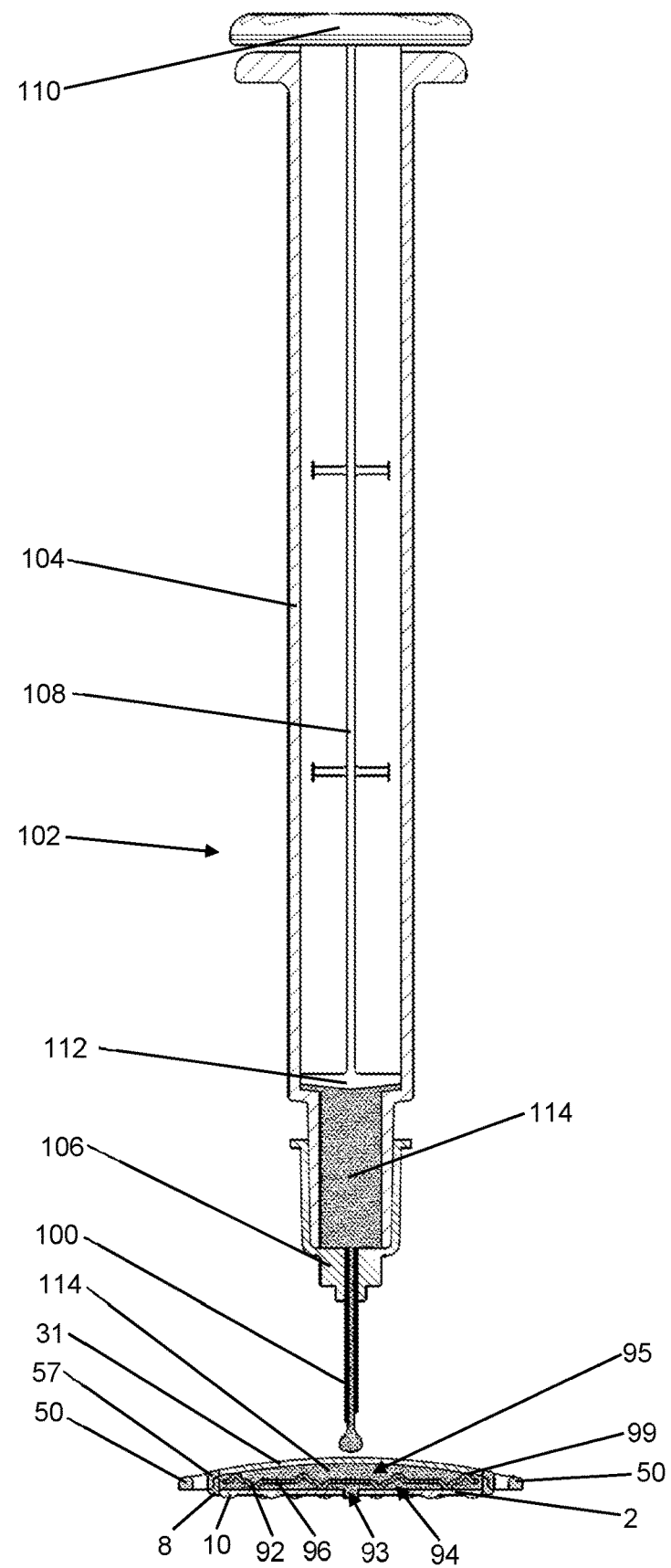
FIG. 30 is a schematic cross-sectional view through the ninth implant and the syringe withdrawn from the ninth implant after filling of the ninth implant.

The lower wall 2 and the upper wall 31 may be elastically expandable. The hollow space 94 may then be elastically deformed or elastically expanded by injection of the liquid 114 into the hollow space 94. The liquid 114 in the hollow space 84 is then under an elastic pressure. Once the hollow space 94 has been filled with the liquid, the injection cannula 100 can be withdrawn from the upper wall 31. In so doing, the upper wall 31 closes automatically. This is shown in FIG. 30.

Figure 31:
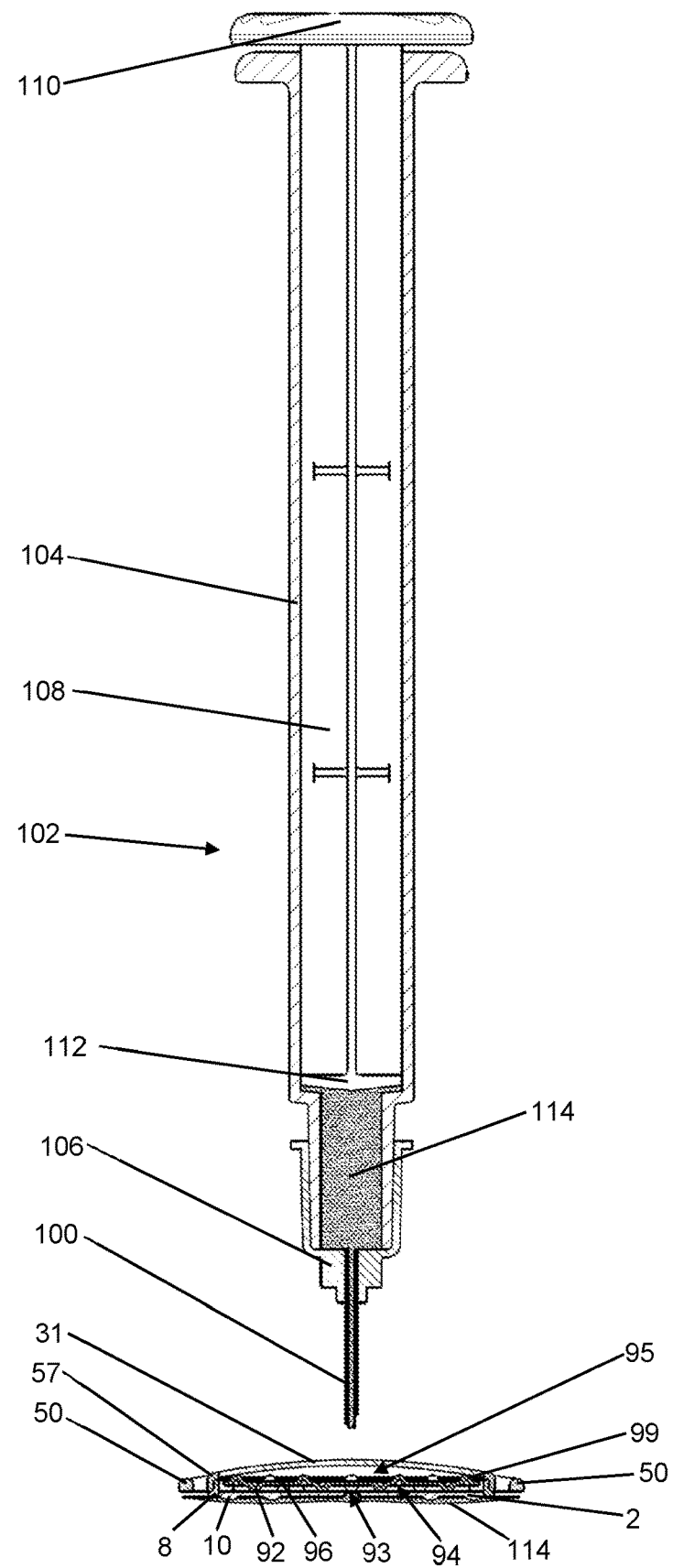
FIG. 31 is a schematic cross-sectional view through the ninth implant and the syringe withdrawn from the ninth implant during exit of liquid from the ninth implant.
Figure 33:
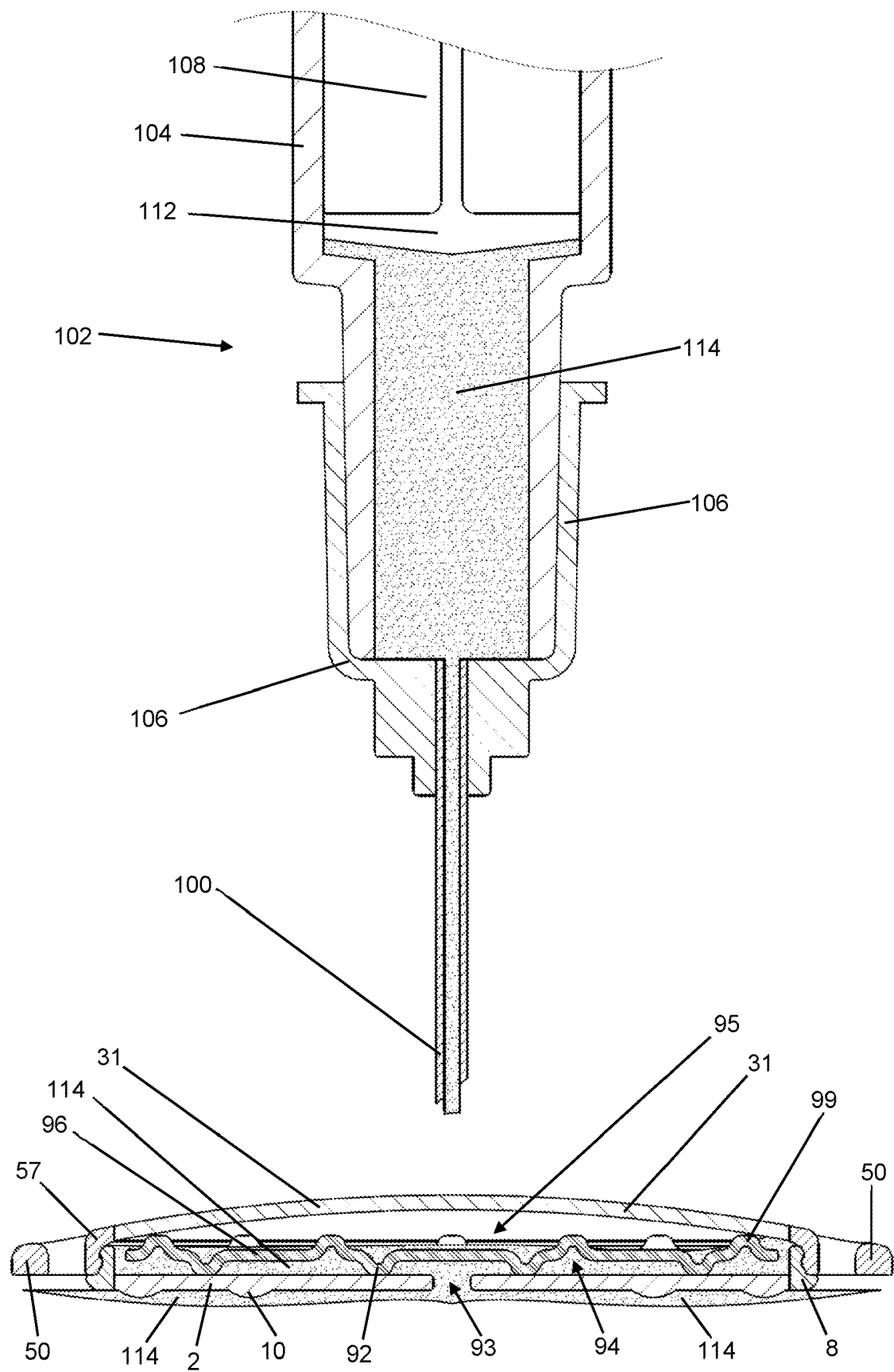
FIG. 33 is a detail view of the ninth implant as an enlarged detail of FIG. 31.

As a result of the elastic pressure of the upper wall 31 and the lower wall, the liquid 114 can be expelled through the feed-through 3 from the hollow space 84 and flow downward through the feed-through 3 (see FIGS. 31 and 33). Before or also after, the implant may be implanted subcutaneously in the region of a joint or at another site to be treated and sutured to soft tissue and fixed in place with the assistance of the lugs 50. After exiting from the hollow space 94, the liquid 114 can be spread and distributed through the feed-through 3 and along the interspace between the lower side of the lower wall 2 and the substrate. Once liquid 114 has ceased flowing out of the hollow space 94, either a pressure may be exerted on the implant in order to overcome back pressure and release further liquid 114 from the implant or new liquid 114 can injected into the interior 95 with the syringe 102.

The features of the invention disclosed in the preceding description, as well as in the claims, figures and exemplary embodiments, may be essential both individually and in any combination for realizing the invention in its various embodiments.

LIST OF REFERENCE SIGNS 1, 31 Upper wall
2, 62, 72 Lower wall
3, 63, 73 Feed-through
4, 34, 84, 94 Hollow space
5, 35, 85, 95 Interior
6, 86, 96 Anti-piercing means
7, 27, 37, 47, 57 Upper rim
8 Lower rim
10, 60 Bump
12 Protruding patterning
14, 24, 34, 44, 54 Latching ring
16 Latching ring
18 Tab
20, 50 Lug
30 Perforated ring
39 Lug/hole
69, 79 Tube
70 Rib
82, 92 Surface patterning
99 Surface patterning
100 Injection cannula
102 Syringe
104 Cartridge
106 Cartridge head
108 Plunger
110 Grip
112 Piston
114 Liquid

The invention claimed is:

1. An implant for local active ingredient release, the implant having an upper wall, wherein the upper wall is closed and disk-shaped and consists of a material which is pierceable with a medical injection cannula using a force of less than 100 N, is self-sealing and is elastically deformable, a lower wall, wherein the lower wall is arranged opposite the upper wall, is disk-shaped, is elastically deformable and the lower wall has at least one feed-through through the lower wall, wherein the at least one feed-through is liquid-permeable, a hollow space which is arranged between the upper wall and the lower wall, an impenetrable anti-piercing means, wherein the anti-piercing means is arranged between the upper wall and the lower wall and is disk-shaped, wherein the anti-piercing means consists of a material which is not pierceable with a medical injection cannula using a force of less than 100 N, wherein the anti-piercing means is at least as large as 50% of an interior surface of the lower wall which delimits the hollow space; and wherein the anti-piercing means has surface patterning on a side facing the lower wall such that the anti-piercing means is spaced apart from the lower wall thereby allowing liquid to flow between the anti-piercing means and the lower wall.

2. The implant according to claim 1, characterized in that the upper wall and the lower wall are connected together via a circumferential rim or are connected together via a circumferential boundary of the anti-piercing means, wherein the upper wall and the lower wall are connected together in liquid-tight manner.

3. The implant according to claim 1, characterized in that the anti-piercing means consists of metal or contains at least 50% of metal and/or
the anti-piercing means is arranged in the hollow space, wherein the anti-piercing means is not firmly connected to the upper wall and the anti-piercing means is arranged on a side of the lower wall which faces the upper wall.

4. The implant according to claim 1, characterized in that the lower wall is pierceable with a medical injection cannula, wherein the lower wall consists of a rubber-elastic plastics material, and/or
the ratio of width to height and of depth to height of the implant is selected from the group consisting of at least 2:1 and at least 3:1.

5. The implant according to claim 1, characterized in that the hollow space is elastically expandable by injection of a liquid, wherein the liquid in the expanded hollow space is expellable with an elastic force from the hollow space through the at least one feed-through.

6. The implant according to claim 1, characterized in that, the lower wall has, on a side opposite the upper wall, protruding patterning which is suitable for distributing a liquid on this external surface, wherein the protruding patterning comprises ribs and/or bumps and/or the at least one feed-through opens into at least one channel on this outer surface of the lower wall and the at least one channel is shaped by the protruding patterning, and/or
a liquid is present in the hollow space, wherein the liquid comprises cyclosporin A, or an active ingredient solution or an ingredient in the solid or semisolid state.

7. The implant according to claim 1, characterized in that
the anti-piercing means is at least as large as 75% of the interior surface of the lower wall which delimits the hollow space, and/or
the anti-piercing means does not rest flush at a circumferential boundary of the anti-piercing means against the internal side of the hollow space.

8. The implant according to claim 1, characterized in that
the implant is disk-shaped and the upper wall forms an upper side of the implant and the lower wall forms a lower side of the implant, wherein the entire external surface of the implant or the entire external surface of the implant apart from a circumferential rim is formed by the upper and the lower wall, and/or
the hollow space has an interior which is delimited by the upper wall and by the anti-piercing means, wherein the interior spaces the upper wall from the anti-piercing means by at least 0.5 mm or by at least 1 mm.

9. The implant according to claim 1, characterized in that
a pressure relief valve is arranged in each of the at least one feed-throughs, which pressure relief valve opens to the outside from a minimum pressure and-opens to the outside from a minimum pressure of at least 20 kPa, and/or
the upper wall and/or the lower wall consists or consist of a rubber-elastic plastics material or, apart from a rim, consists or consist of a rubber-elastic plastics material, wherein, after piercing by and withdrawal of a medical injection cannula, the rubber-elastic plastics material of the upper wall contracts again and closes liquid-impermeably.

10. The implant according to claim 1, characterized in that
the anti-piercing means has at least one liquid-permeable opening, wherein the at least one opening has a free cross-section of a maximum of 0.5 mm, and/or
the anti-piercing means has surface patterning on the side facing the upper wall.

11. The implant according to claim 1, characterized in that
the anti-piercing means is firmly connected to the lower wall and/or,
on an upper side which faces the upper wall, the anti-piercing means has a concave shape and/or has a protruding boundary, and/or
the implant has one or more lugs by which the implant can be sutured to soft tissue.

12. A method for filling an implant according to claim 1, characterized by the steps:
A) providing the implant and a syringe filled with a liquid, wherein the syringe has a medical injection cannula,
B) piercing the upper wall with the medical injection cannula of the syringe,
C) injecting liquid from the syringe through the medical injection cannula and into the hollow space of the implant,
D) spreading the liquid in the hollow space, wherein the liquid flows up to the at least one feed-through, and,
E) optionally, elastic expansion of the hollow space by injection of the liquid.

13. The method according to claim 12, characterized in that
the method does not involve any medical treatment of a human or animal body and/or the liquid is not delivered to a human or animal body in the context of the method.

14. The method according to claim 12, characterized in that,
in step B), the tip of the medical injection cannula is inserted through the upper wall to such an extent that it comes into contact with the anti-piercing means, wherein an orifice at the tip of the medical injection cannula is then located in an interior of the hollow space, wherein the interior of the hollow space is arranged between the anti-piercing means and the upper wall.

15. The method according to claim 12, characterized in that
the following steps F) and G) and optionally H) proceed after step E):
F) withdrawal of the medical injection cannula from the hollow space and from the upper wall and
G) liquid-tight closure of the upper wall by rubber-elastic recovery of the upper wall, and optionally
H) compression of the hollow space due to the elastic restoring force of the elastically expanded hollow space and expulsion of the liquid from the hollow space through the at least one feed-through.

* * * * *